United States Patent
Desai et al.

(10) Patent No.: US 10,930,372 B2
(45) Date of Patent: Feb. 23, 2021

(54) SOLUTION FOR DRUG DISCOVERY

(71) Applicant: NORTHROP GRUMMAN SYSTEMS CORPORATION, Falls Church, VA (US)

(72) Inventors: Sanjiv Desai, Stone Ridge, VA (US); Sreelatha Ghanta, Asburn, VA (US)

(73) Assignee: Northrop Grumman Systems Corporation, Falls Church, VA (US)

( * ) Notice: Subject to any disclaimer, the term of this patent is extended or adjusted under 35 U.S.C. 154(b) by 992 days.

(21) Appl. No.: 14/873,837

(22) Filed: Oct. 2, 2015

(65) Prior Publication Data

US 2017/0098032 A1 Apr. 6, 2017

(51) Int. Cl.
*G16B 50/00* (2019.01)
*G16B 20/00* (2019.01)
*G16H 10/20* (2018.01)

(52) U.S. Cl.
CPC ............. *G16B 50/00* (2019.02); *G16B 20/00* (2019.02); *G16H 10/20* (2018.01)

(58) Field of Classification Search
None
See application file for complete search history.

(56) References Cited

U.S. PATENT DOCUMENTS

| 2005/0060305 | A1* | 3/2005 | Hopkins | G06Q 50/22 |
| 2014/0121120 | A1* | 5/2014 | Chen | G06F 19/12 |
| | | | | 506/8 |
| 2014/0279721 | A1 | 9/2014 | Siegel et al. | |

FOREIGN PATENT DOCUMENTS

WO 2014018739 A1 1/2014

OTHER PUBLICATIONS

International Search Report and Written Opinion of corresponding application No. PCT/US2016/054592 dated Dec. 7, 2016, all enclosed pages cited.

\* cited by examiner

*Primary Examiner* — Rachelle L Reichert
(74) *Attorney, Agent, or Firm* — Burr & Forman, LLP

(57) ABSTRACT

A drug discovery system may include a data platform and a drug discovery module. The data platform may be scalable to include a plurality of data sources. The data sources may include at least a clinical research database providing results of clinical trials. The drug discovery module may include a pharmaco-genomic mapper configured to provide a mapping of drugs to biomarkers based on extraction of information from the data sources, and a genome connect module configured to provide a mapping of biomarkers to diseases based on extraction of information from the data sources. The drug discovery module may include processing circuitry configured to provide a potential drug to disease link based on the mapping of drugs to biomarkers and the mapping of biomarkers to diseases using the biomarkers as a bridge.

20 Claims, 9 Drawing Sheets

US 10,930,372 B2

SOLUTION FOR DRUG DISCOVERY

TECHNICAL FIELD

Example embodiments generally relate to healthcare information management, and more particularly, to the employment of a system for healthcare information management in connection with drug discovery.

BACKGROUND

The healthcare industry provides goods and services to treat patients with curative, preventive, rehabilitative, and palliative care. The modern healthcare sector is divided into many sub-sectors, and depends on interdisciplinary teams of trained professionals and paraprofessionals to meet health needs of individuals and populations. The healthcare industry is one of the world's largest and fastest-growing industries.

As the healthcare industry grows, public attention is focused on decreasing healthcare costs both in aggregate, and to the individual. Healthcare costs are often higher when treating later stage diseases or illnesses. Thus, part of the effort to reduce or control healthcare costs has been focused on the treatment of diseases or illnesses at an earlier stage. Earlier stage treatment requires earlier stage identification of such diseases or illnesses.

With the advent of "big data" analytics, opportunities may arise to extract useful information from massive amounts of information related to healthcare in order to facilitate earlier stage disease identification and treatment. However, the specific tools and platforms that are used to employ such analytics are still being developed and identified. As these tools are developed, the ability to provide personalized healthcare that is tailored to the individual may emerge and facilitate early stage disease detection and treatment. Moreover, in some cases, the ability to predict specific conditions to be watchful for relative to a specific individual may be provided. Individual healthcare quality and effectiveness may therefore improve, and healthcare cost and quality in the aggregate may also improve.

SUMMARY

In accordance with an example embodiment, a system for personalized healthcare is provided. The system may include a data platform, an analytics platform, a modeling component and a user interface component. The data platform, like the entire system, may be scalable. In particular, the data platform may be scalable to include a plurality of data sources that can be analyzed via the analytics platform. Various different analytical tools can be plugged into the system to analyze the data sources to extract data that, using the modeling component, can be used to identify potentially useful information related to healthcare. The system may be robust in terms of the amount and types of data that are accessible, and the tools for extracting useful information for individual patients, for clinicians, and for researchers. In an example embodiment, one of those tools may be a drug discovery module that is configured to discover drug to biomarker to disease links that were previously unknown.

In accordance with an example embodiment, a drug discovery system is provided. The system may include a data platform and a drug discovery module. The data platform may be scalable to include a plurality of data sources. The data sources may include at least a clinical research database providing results of clinical trials. The drug discovery module may include a pharmaco-genomic mapper configured to provide a mapping of drugs to biomarkers based on extraction of information from the data sources, and a genome connect module configured to provide a mapping of biomarkers to diseases based on extraction of information from the data sources. The drug discovery module may include processing circuitry configured to provide a potential drug to disease link based on the mapping of drugs to biomarkers and the mapping of biomarkers to diseases using the biomarkers as a bridge between the mappings.

In another example embodiment, a method of drug discovery is provided. The method may include accessing information associated with genetic markers from a data platform scalable to include a plurality of data sources where the data sources include at least a clinical research database providing results of clinical trials. The method may further include employing a drug discovery module to provide a mapping of drugs to biomarkers based on the information, and employing the drug discovery module to provide a mapping of biomarkers to diseases based on the information. The drug discovery module may include processing circuitry configured to provide a potential drug to disease link based on the mapping of drugs to biomarkers and the mapping of biomarkers to diseases using the biomarkers as a bridge between the mappings.

BRIEF DESCRIPTION OF THE DRAWINGS

Figure 1:
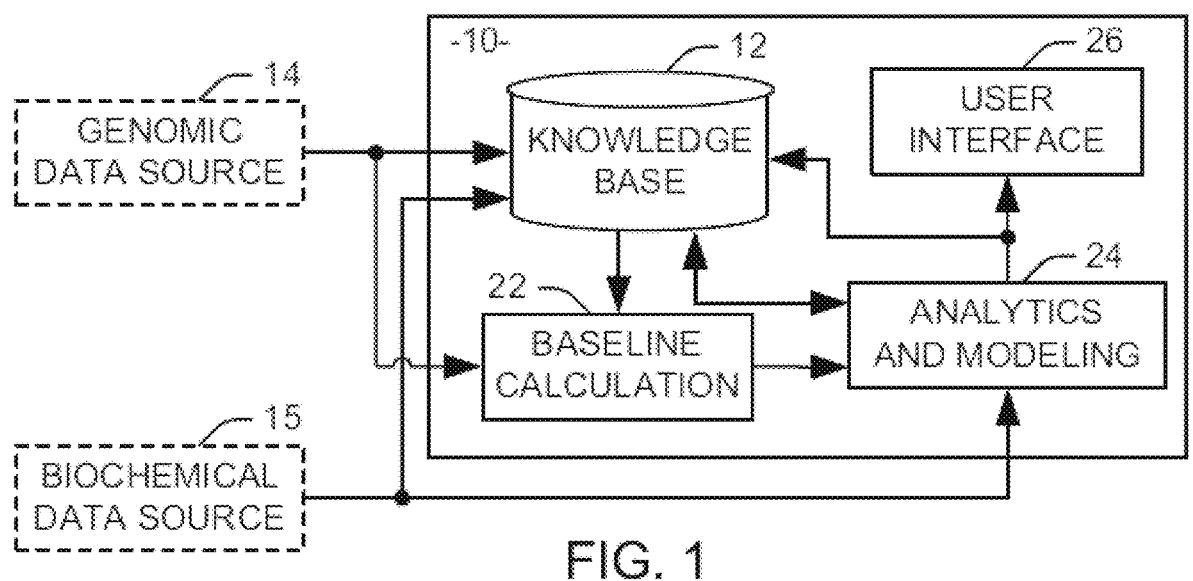
Figure 2:
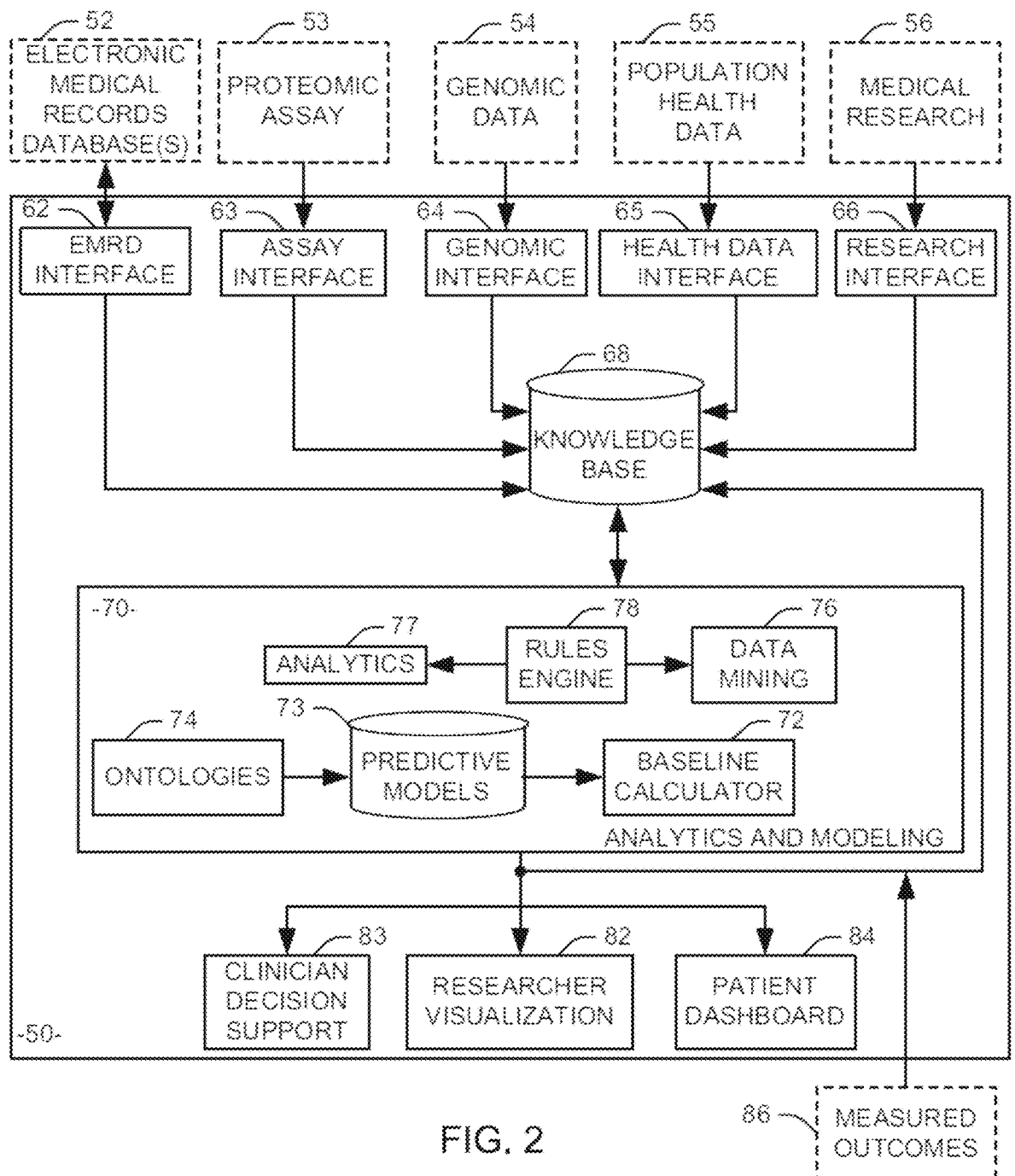
Figure 3:
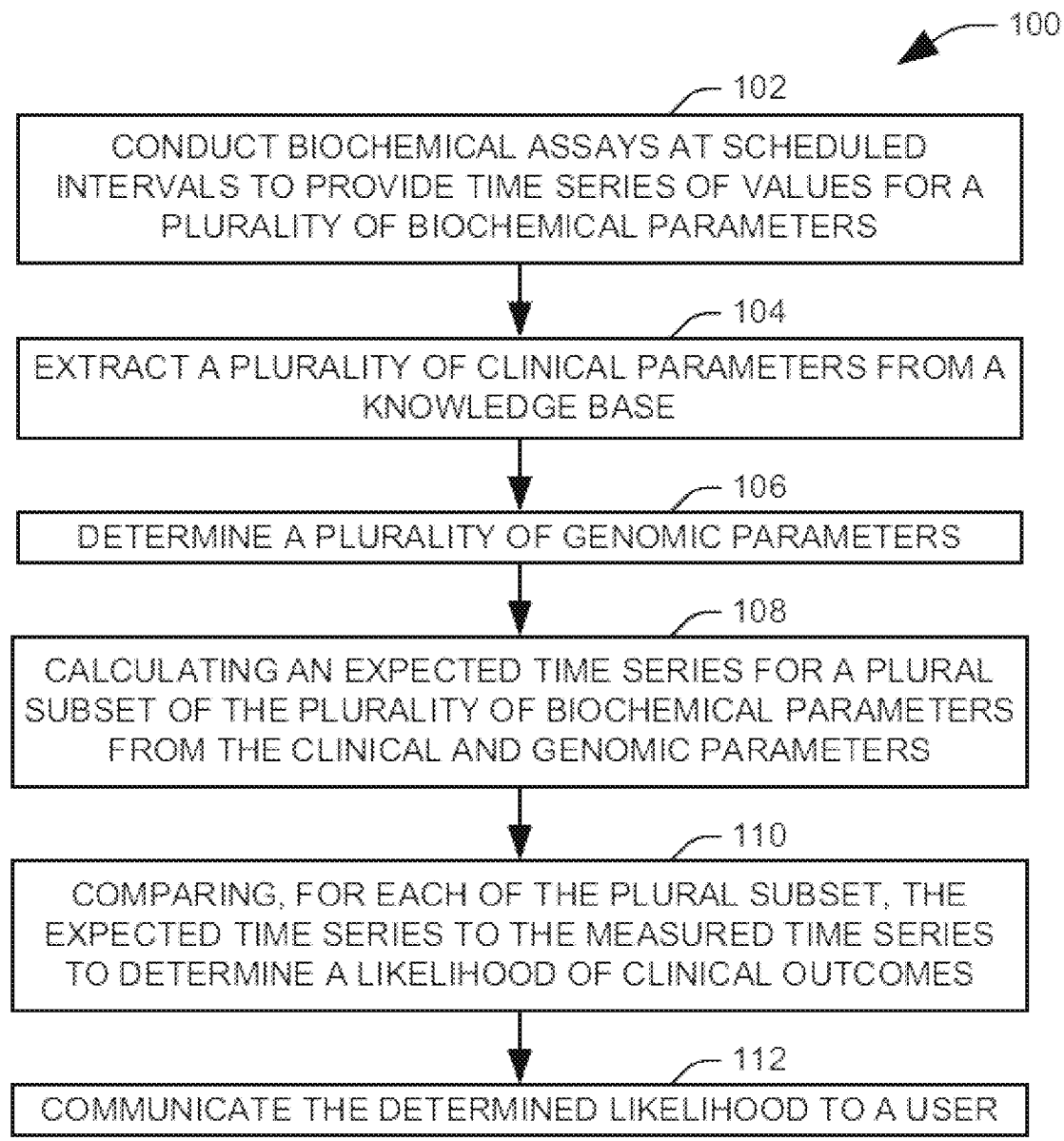
Figure 4:
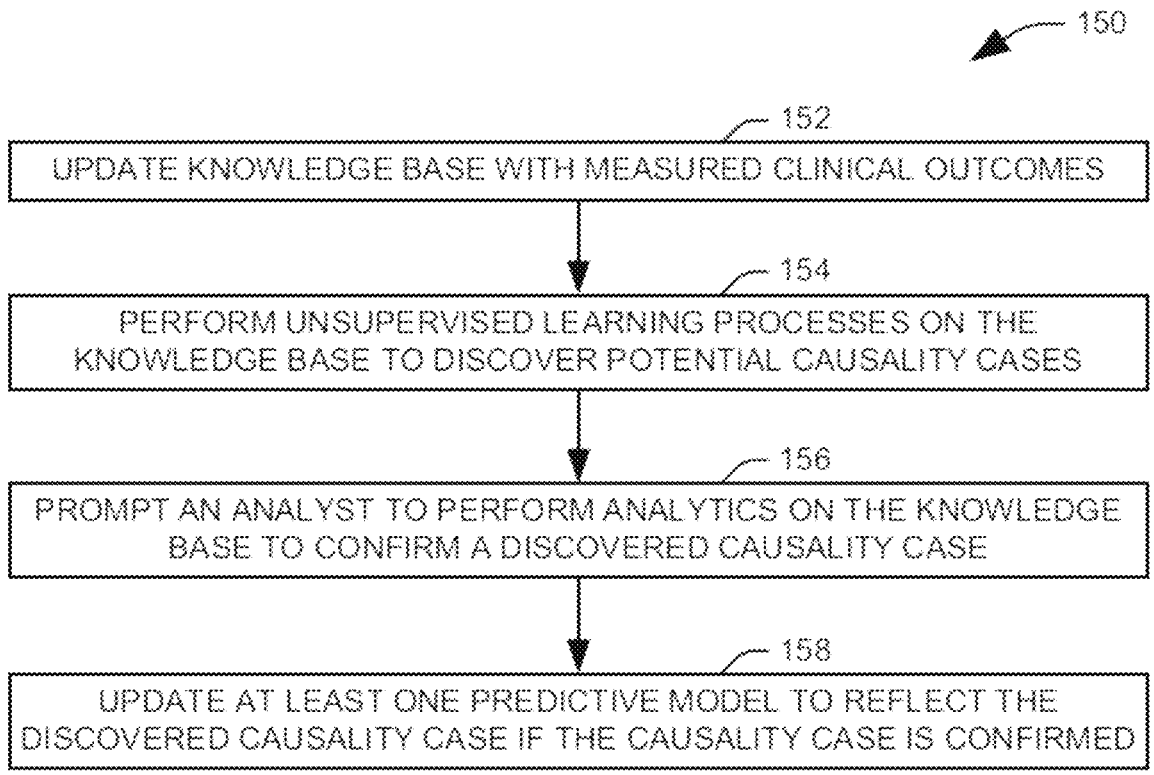
Figure 5:
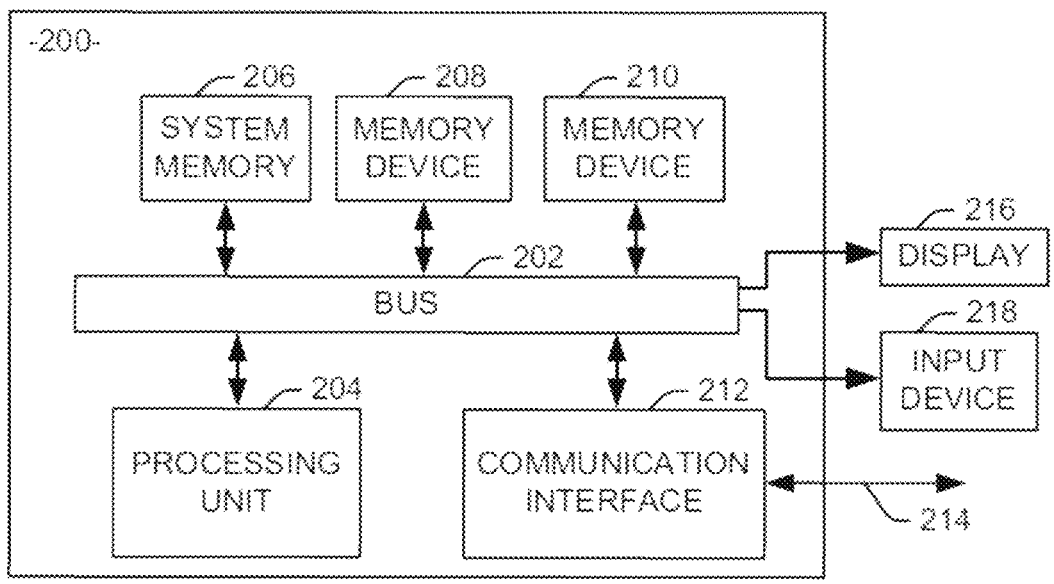
Figure 6:
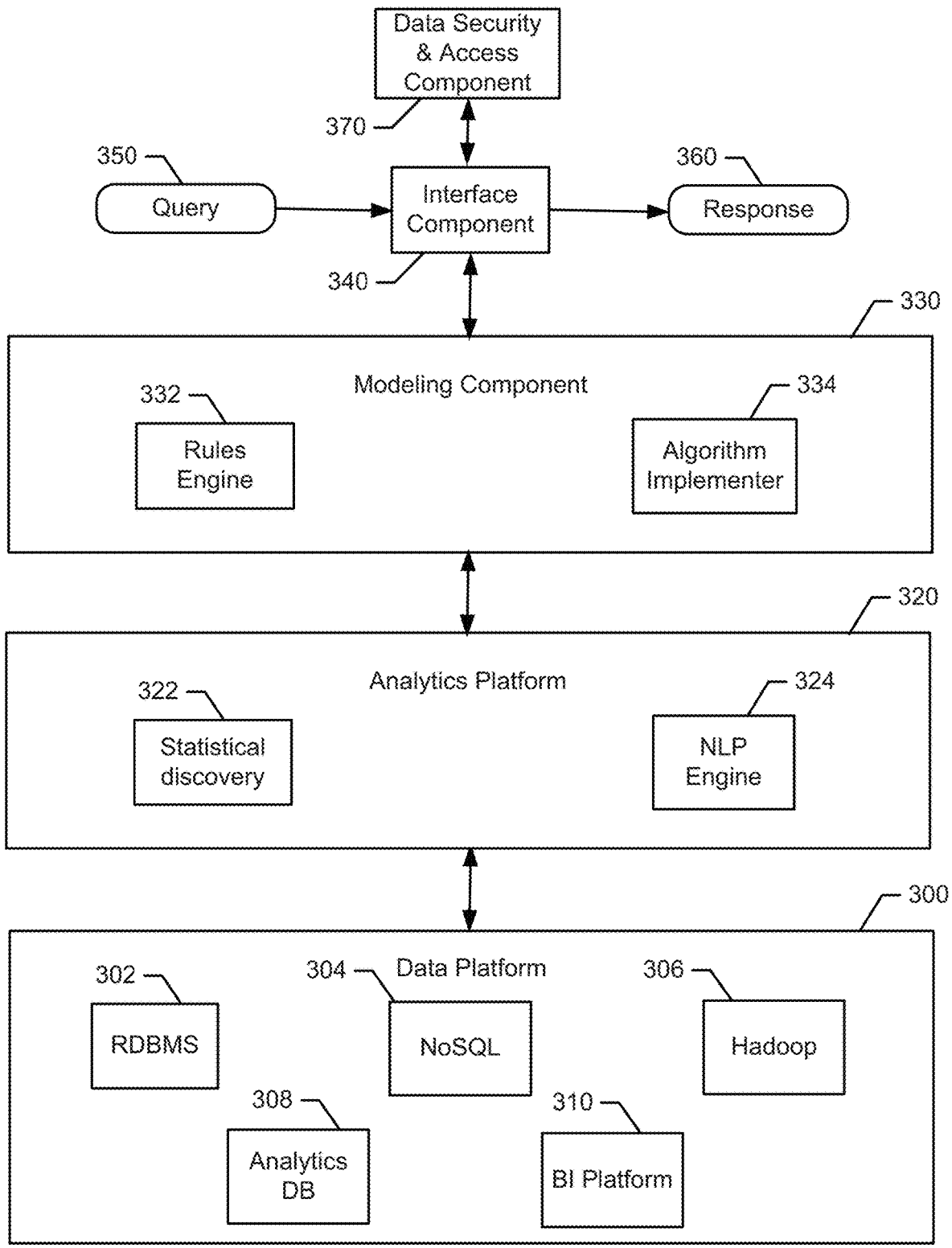
Figure 7:
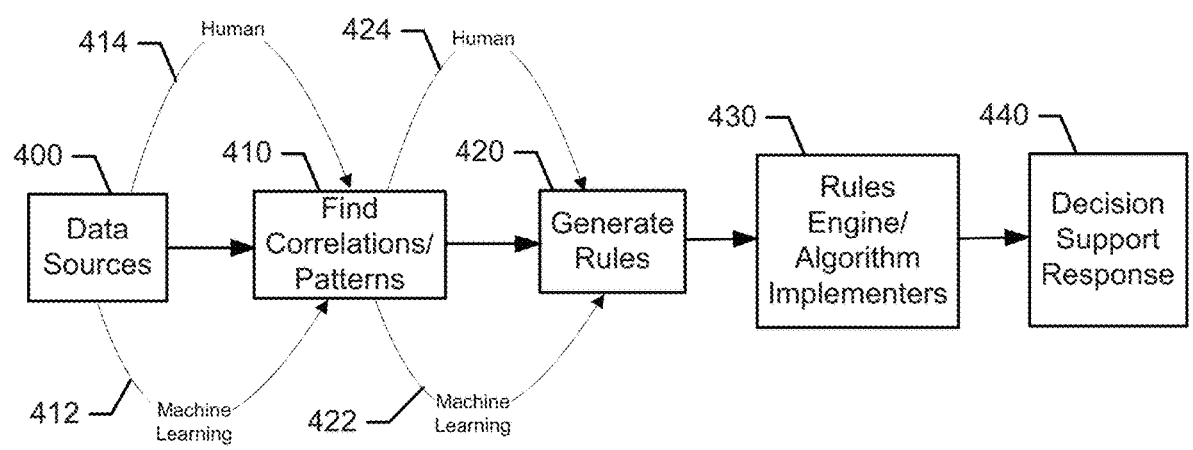
Figure 8:
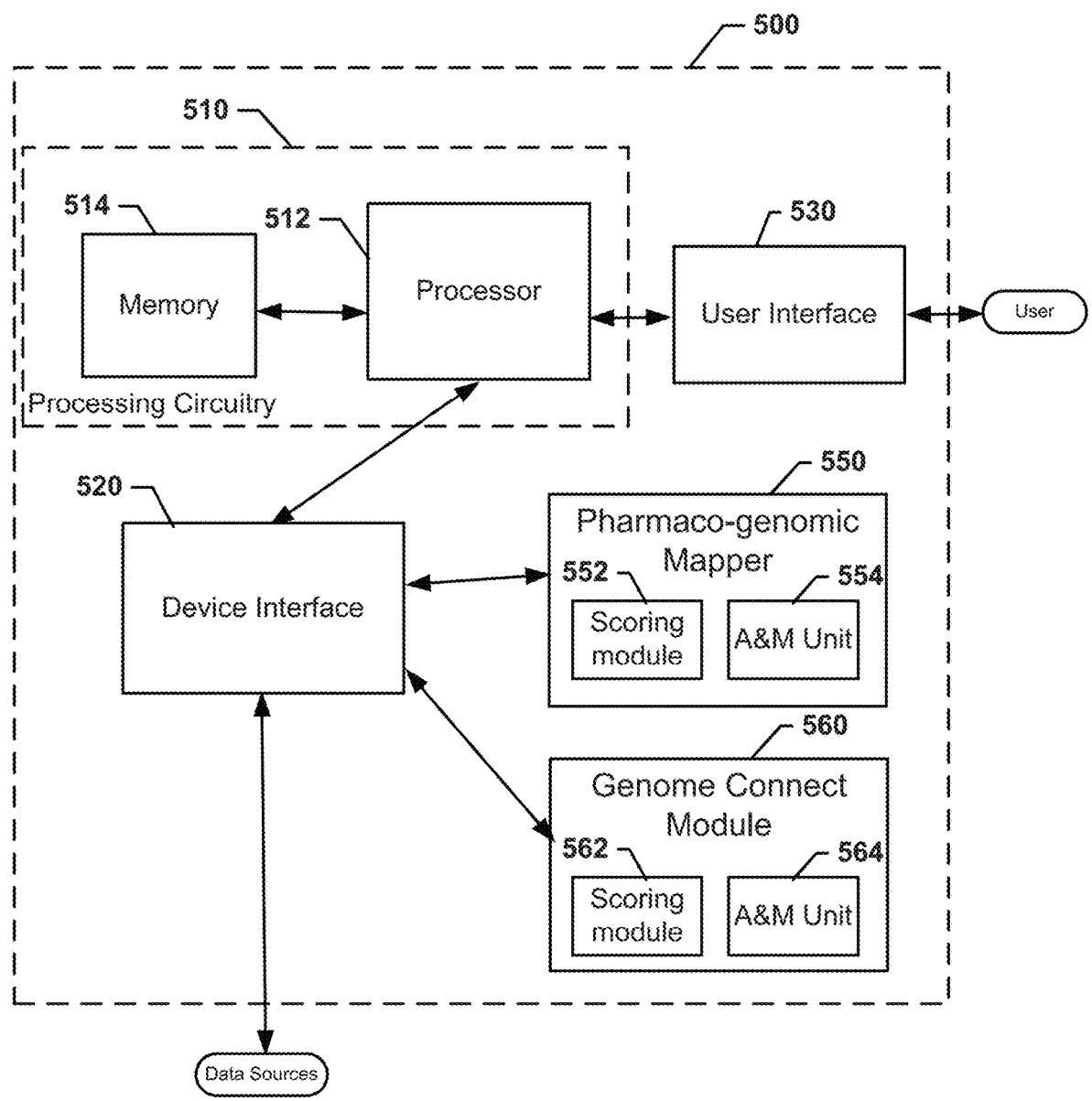
Figure 9:
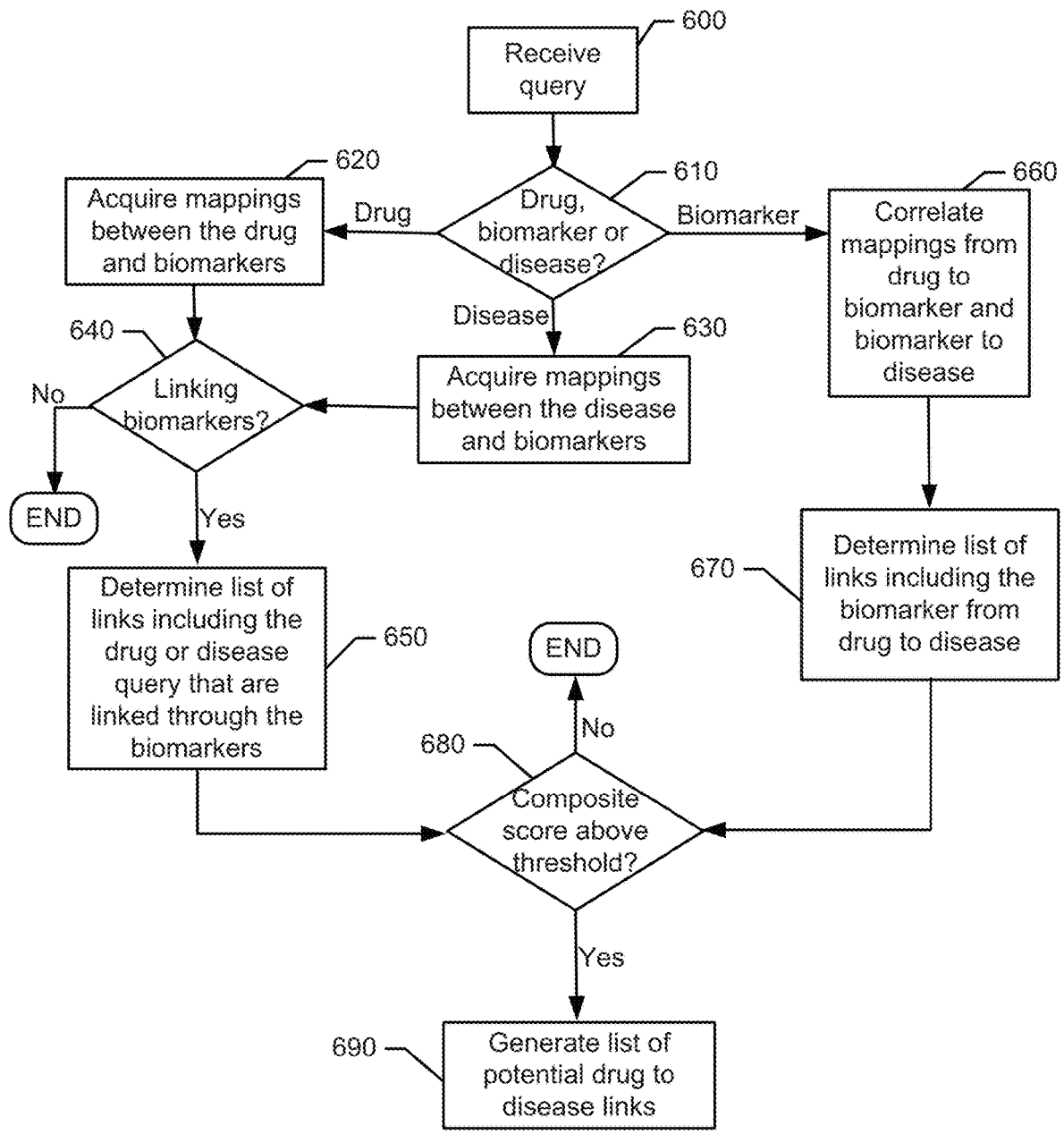
Figure 10:
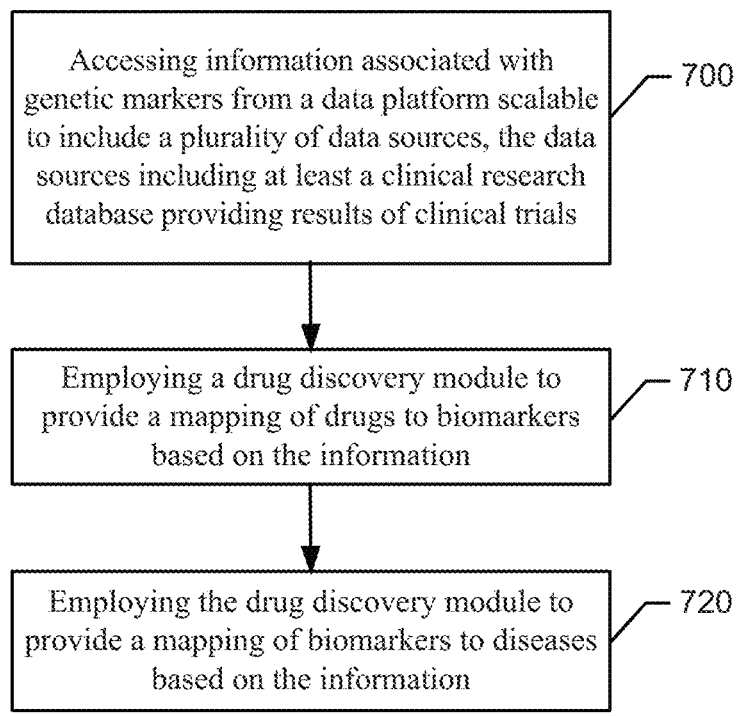

Having thus described some example embodiments in general terms, reference will now be made to the accompanying drawings, which are not necessarily drawn to scale, and wherein:

FIG. 1 illustrates block diagram of a learning healthcare system in accordance with an example embodiment;

FIG. 2 illustrates a block diagram of one implementation of a learning healthcare information processing system in accordance with an example embodiment;

FIG. 3 illustrates a block diagram of a method for providing personalized healthcare support in accordance with an example embodiment;

FIG. 4 illustrates a block diagram of a method for discovering and applying new causality cases in a learning healthcare system in accordance with an example embodiment; and FIG. 5 is a schematic block diagram illustrating an exemplary system of hardware components capable of implementing examples of the systems and methods disclosed in FIGS. 1-4 in accordance with an example embodiment;

FIG. 6 is a block diagram of a cloud-based platform for implementing an example embodiment;

FIG. 7 illustrates a block diagram of the mechanisms and platforms associated with practicing example embodiments;

FIG. 8 illustrates a drug discovery module in accordance with an example embodiment;

FIG. 9 illustrates a block diagram of operations associated with an example algorithm for facilitating drug discovery in accordance with an example embodiment; and FIG. 10 illustrates a method of providing drug discovery in accordance with an example embodiment.

DETAILED DESCRIPTION

Healthcare in the many nations is driven by medical protocols, which are guidelines for when and how to perform diagnostic and clinical activities on an individual.

These protocols, however, are created with, at best, superficial reference to any significant knowledge of the individual. In accordance with an example embodiment, it has been determined that genomics can be helpful in customizing care, and that genomics data can sometimes be supplemented with other data that provide more insight into ones health condition at the time of the measurement to further customize care. Genomics can be helpful in relation to identifying risk relative to development of a condition, while other measurements may be about present health status.

Accordingly, it has been determined that data about an individual—derived from proteomics and other sources—can allow for a new type of medical protocol. This protocol adapts to deep medical knowledge of an individual, both their current medical and proteomic state and their own trend and history over time, as a replacement for today's medical protocols that are rigid and rely on generalizations based on populations, rather than the medical state of an individual. The practice of medicine in accordance with such new, individualized medical protocols is expected to provide significant cost savings while simultaneously improving average individual health.

To facilitate the type of individualized medical protocols described above, a system for closed loop information processing has been developed. The system may be referred to as a learning health system since the system can be dynamically updated with new data, analytical tools, models and interface mechanisms in order to allow the system to continuously update or learn how to better provide useful healthcare tools and information. The system takes a layered approach to developing a structure for performing analytics over massively large amounts of diverse data. Multiple specifically configured analytic and modeling tools are employed for extracting and analyzing data of different types and in different forms to provide useful information to the user. Additionally, the same system can be used to provide different useful outputs to different users. For example, an individual patient can receive information about his/her risk and potential treatment options for specific diseases or conditions. Likewise, a clinician can receive similar information for a particular patient. However, researchers may also be enabled to extract useful information from the system for various purposes. One such purpose may be the discovery of drugs that may be useful in treatment of specific diseases.

In an example embodiment, biomarkers may be used as a bridge to connecting drugs to diseases that such drugs may be effective to treat. Biomarkers are values, characteristics or variables (including traceable substances) that can be objectively measured and evaluated as an indicator or normal biological processes, pathogenic processes or pharmacological responses to a therapeutic intervention. The biomarkers could be, for example, biochemical biomarkers or genetic markers. Biomarkers may be used in clinical trials to identify the effectiveness of a drug. In such trials, data is gathered regarding a plurality of biomarkers that are generated responsive to taking a drug or drugs involved in the trial, which is typically focused on a particular disease or condition. Drug candidates and biomarker candidates are evaluated and, when desirable matches can be identified (i.e., when positive biomarkers for the disease or condition of interest are generated), a new drug for treatment of a particular disease may be identified. However, drug and biomarker candidates that do not yield desirable matches are typically ignored. Thus, in most cases large amounts of data regarding drugs and corresponding biomarkers is simply ignored or wasted.

In an example embodiment, clinical trial data for unmatched drug and biomarker candidates is used (as wells as the clinical trial data for matched drug and biomarker candidates) to generate a comprehensive drug to biomarker mapping. Information from various data sources can also be used to identify biomarker to disease mapping such that links between drugs and diseases can be made. The drug discovery capabilities may be provided via a module dedicated to the extraction of useful data for defining appropriate mappings, and the module may be a component of a larger learning health system such as that which will be described in herein.

FIG. 1 illustrates a learning health system 10 in accordance with an example embodiment. It will be appreciated that the system can be implemented as machine executable instructions stored on a set of at least one non-transitory computer readable medium and executed by an associated processor, dedicated hardware, or a combination of dedicated hardware and software components. The system 10 includes a knowledge base 12 storing a record for each of a population of patients. The knowledge base 12 can include data received from one or both of a genomic data source 14, representing a genetic mapping of an individual to locate genetic markers, and a biochemical data source 15, representing the levels of various biochemical parameters for the individual as derived from biochemical assays. In accordance with an aspect of an example embodiment, the biochemical assays can be scheduled at regular intervals, such that even healthy patients are encouraged to provide a usable time series of biochemical parameters.

Accordingly, each record can include a time series of values for each a plurality of biochemical parameters taken from biochemical assays performed at scheduled intervals, a plurality of genetic markers, and a plurality of clinical parameters associated with the patient. The plurality of clinical parameters can be extracted, for example from electronic health record databases and include previous diagnoses and procedures, clinical observations, longitudinal biometric parameters (e.g., age, weight, blood pressure, temperature, glucose levels, etc.), and a family medical history. It will be appreciated that the population of patients can include, for each of a plurality of conditions of interest, a set of patients having the condition and a set of patients not having the condition. In addition to patient records, the knowledge base 12 can also contain statistics representing incident rates and measured outcomes for various disorders as well as data on causal links between available parameters and conditions drawn from medical research. In one implementation, a research interface (not shown) can be provided for extracting data from available medical research, including an information extraction component to reduce an unstructured source of research, such as a journal article, into a template compatible with the knowledge base.

A baseline calculation component 22 is configured to calculate, for a given patient, an expected time series for a patient's biochemical parameters from at least the clinical parameters and the genomic parameters associated with the patient. While the system 10, evaluates patients for a large number of conditions in parallel based on the biochemical assays, it will be appreciated that not every biochemical parameter is relevant to every situation and patient. Accordingly, the baseline calculation component 22 may selectively calculate an expected time series for each of a plural subset of the available biochemical parameters to preserve processing resources.

An analytics and modeling component 24 is configured to determine a deviation of the time series of values from the calculated expected time series and apply the deviation as an input to one or more predictive models associated with respective conditions of the plurality of conditions. Each predictive model can be derived from data in the knowledge base 12 associated with each of the set of patients having the condition and the set of patients not having the condition. For example, the predictive models can include appropriate supervised learning algorithms, such as regression models, artificial neural networks, support vector machines, and statistical classifiers, trained on data from the knowledge base. Each predictive model predicts a likelihood of one of a plurality of disorders according to deviations between the measured biometric parameters and the baseline from the deviation. For example, the predictive model can operate on one or more of a distance metric (e.g., Euclidian, Mahalanobis, Manhattan), difference between the measured and expected time series can be used as a predictive feature. Alternatively, the difference in the time series across a number of most recent data points can be used as features. In general, it will be appreciated that a number of descriptive statistics representing differences between two time series can be calculated, and any of these measures may be useful as a predictive feature. It will be appreciated that a given model can include parameters beside the calculated deviation as well, and that these additional parameters can be drawn from the knowledge base. In one implementation, the results of the predictive modeling can be supplemented with an actual course of treatment and a measured clinical outcome and fed back to the knowledge base 12 for use in generating addition causality cases.

In one implementation, the analytics and modeling component 24 can include a data mining component (not shown) configured to perform a plurality of unsupervised learning algorithms on the knowledge base 12 to determine at least one causality case relating one of the clinical parameters and the genomic parameters to the condition. The determined causality case can, once confirmed by subject matter experts, be used to refine existing predictive models or generate new predictive models. To facilitate review of the newly generated causality cases, the analytics and modeling component 24 can also include an analytics component (not shown) available to the user through a user interface 26 and configured to retrieve data from the knowledge base 12 and an associated database (not shown). Under the guidance of a subject matter expert, the analytics component can run various queries on the knowledge base 12 and the associated database to provide evidence supporting or refuting a given causality case. In one implementation, the analytics and modeling component 24 also includes a rules engine (not shown) that evaluates causality cases determined by the data mining component, according to an associated set of rules, to determine which variables, associated with the causality cases, present a highest likelihood of providing actionable results if evaluated with the analytics component. By limiting the analysis to parameters believed to be relevant, this rules engine can be used to conserve processing resources and decrease the likelihood of false positives in determining interrelationships among the data stored in the knowledge base 12.

The user interface 26 is configured to provide the determined likelihood that the patient has the condition to a user. The user interface 26 can include visualization tools to allow the user to see a graphical comparison of the expected time series of biochemical parameter values and an actual time series of biochemical parameter values. In one implementation, the user interface 26 includes a patient dashboard (not shown) configured to communicate each of the determined likelihood of the condition, a healthcare treatment course of action, and/or a scheduled next biochemical assay. Accordingly, the patient can be instructed to enter the healthcare system at an appropriate time based on the biochemical analysis. The patient dashboard may also include links to information about any diagnosed disorders and recommended treatment option.

The user interface 26 can also include a clinician decision support component (not shown) configured to communicate a recommended protocol of care to a clinician based on the determined likelihood that a patient has a condition. By making the data from the knowledge base 12 and predictive models available to all stakeholders in the healthcare system, the user interface 26 can ensure transparency of the recommended courses of actions to clinicians and patients and ensure that researchers have easy access to data stored in the knowledge base to allow for the generation of new causality cases and predictive models.

FIG. 2 illustrates one implementation of a learning healthcare information processing system 50 in accordance with an example embodiment. In the illustrated implementation, the system 50 receives data from a plurality of data sources 52-56 external to the system, indicated in a dashed outline, through respective data interfaces 62-65 and processes that data to provide recommendations to patients, clinicians, and researches based on accumulated data from these resources. A first data source 52 includes electronic medical record databases, with each electronic medical record database containing medical data for a plurality of patients comprising, for example, previous diagnoses and procedures, clinical observations, longitudinal biometric parameters, and a family medical history. Examples of electronic medical record databases that could be compatible with the information processing system can include the Armed Forces Health Longitudinal Technology Application (AHLTA), the Veterans Health Information Systems and Technology Architecture (VISTA), and similar such databases maintained by large healthcare organizations with a significant patient base. Records from these databases can be provided through an electronic medical record database (EMRD) interface 62 to convert the retrieved records to an appropriate format for a knowledge base 68 associated with the healthcare information processing system 50. In one implementation, the full record stored in the electronic medical record database is truncated by the interface to a set of clinically relevant observations.

The data sources can also include a biometric assay taken from a large population of patients. In the illustrated implementation, a proteomic assay 53 is utilized, but it will be appreciated that other biometric assays can also utilized, including pharmacogenomic assays, metabolomic assays, epigenomic assays, as well as interactomic, transcriptomic, and microbiomic data. In one implementation, the proteomic assay 53 can detect around ten thousand proteins and be administered at scheduled intervals to provide a time series of blood levels for each of the ten thousand proteins. An assay interface 63 may be configured to format the assay data for the knowledge base 68 and associate identifying information of the assays with corresponding patient records in the knowledge base. The assay interface 63 may also be configured to normalize the proteomic data to a scale utilized by the knowledge base 68. In one implementation, the proteomic assay 53 can be reduced to a vector of clinically important features to be provided to the knowledge base 68, with the full assay compressed and stored in a separate mass storage with time-stamped line from the patient file to the full assay.

The system 50 can also utilize genomic data 54 from a population of patients. For example, the genomic data 54 can be captured for each patient via an appropriate assay and provided to the system through a genomic interface 64. The genomic interface 64 extracts known genetic markers from the genome, formats the extracted data for the knowledge base 68 and associates identifying information of the genetic information with corresponding patient records in the knowledge base 68, for example, via a link from the patient record to the extracted markers.

Information and statistics from population health data sources 55 can be provided through a health data interface 65. Population health data sources 55 include, for example, structured or semi-structured data representing incident rates and measured outcomes for various disorders. Examples of population health data sources 55 can include the Surveillance, Epidemiology, and End Results (SEER) program maintained by the National Cancer Institute, the Behavioral Risk Factor Surveillance System (BRFSS) maintained by the Centers for Disease Control and Prevention, the Healthcare Cost and Utilization Project (HCUP) maintained by the Agency for Healthcare Research and Quality, and the Food and Drug Administration Adverse Event Reporting System (FAERS). The health data interface 65 may be configured to convert the structured and semi-structured data maintained in these resources into an appropriate format for a knowledge base 68 associated with the system 50.

Finally, data concerning causality factors for various disorders can be captured from medical research data 56 (or literature) and provided to the knowledge base 68 through a research interface 66. Exemplary sources of medical research data (or literature) can include the Medline collection from the National Library of Medicine, the PubMed collection, the GenBank sequence database, and the Gene Expression Omnibus repository maintained by the National Center for Biotechnology, the ArrayExpress and InterPro databases maintained by the European Bioinformatics Institute, the ImmPort immunology database and the Database for Annotation, Visualization, and Integrated Discovery maintained by the National Institute of Allergy and Infectious Diseases, and the UniProt knowledge bases, as well as Internet publications, such as Wikipedia, WebMD, health organization websites, and similar information sources. Since the medical research data 56 can include unstructured data, the research interface 66 can include an information extraction component to reduce an unstructured source of research, such as a journal article, into a format compatible with the knowledge base 68. The information extraction component may be configured to break down the unstructured source into individual words or phrases, interpret the context and meaning of the various words or phrases, and use the extracted information to generate a template representing the unstructured source. In one implementation, the generated template can be reviewed by a human expert in a field relevant to the unstructured source to ensure that the information provided to the knowledge base 68 is accurate.

The knowledge base 68 can be implemented as a massively parallel system to provide a low response time and significant scalability for increasing amounts of data. In one implementation, the knowledge base 68 can include a plurality of geographically remote regional caches, such that data associated with a given patient population is easily and quickly accessible to local clinicians. Each cache is operatively connected to a master knowledge base to allow for analysis of the data in aggregate for researchers, and can be fed data by the master knowledge base according to scheduled appointments. Requests from emergency rooms and other unscheduled sources of care can be prioritized to allow real-time or near real-time access to patient information. Information in the caches can be replaced such that data that has been least recently used is replaced. The knowledge base 68 may store any or all of clinical observations, proteomics, and genomics from various patients, including data for both a healthy population and a population of individuals that have disease syndromes, allergic reactions, or some other undesirable clinical outcome. The knowledge base 68 may include a mixture of active data in the knowledge base, for example, triggers supported by a notification subsystem, and a rule base using a scalable rules engine.

In accordance with an aspect of an example embodiment, an analytics and modeling component 70 can interact with the knowledge base 68 to determine relationships among the data. The function of the analytics and modeling component 70 can be roughly divided into what is referred to herein as "forward analytics," in which the likelihood of any of a variety of conditions for a given patient can be predicted by comparing data associated with the patient to data from the larger population, and "backwards analytics," in which data from a large population of patients is mined to determine relationships between clinical parameters and identified conditions.

In one example of a forward analytics process, a baseline calculator 72 can be configured to calculate, for a given patient, an expected longitudinal progression of a biometric parameter, such as the levels of clinically relevant proteins from the proteomic assays 53. In general, the baseline is determined according to an amalgamation of biometric parameters recorded for cohorts of similarly situated patients, that is, patients who either live or work in the same location as the patient, have similar genetic markers, have similar medical histories, or otherwise have clinically relevant parameters in common with the patient. The baseline can be calculated, for example, via one or more statistical models that utilize this data to determine what an appropriate level or range of levels for each of a plurality of clinical relevant biometric parameters would be for the patient given his or her medical history, including not only diagnoses and conditions, but also longitudinally recorded parameters such as weight, blood pressure, and glucose levels, the patient's genetics, and the patient's biographical parameters, such as age and location of residence.

It will be appreciated that the knowledge base 68 is expected to include a large number of patient records. Accordingly, in one implementation, for each protein, the knowledge base 68 can simply be queried to return all or a predetermined number of records having all or a threshold number of biometric parameters relevant to establishing a baseline for that protein within a defined range around the patient's values for the biometric parameters. The time series for the protein can be averaged across all retrieved records to provide the baseline.

Once the baseline for biometric parameters has been calculated, each of the calculated baselines and a measured plurality of series of biometric parameters can be provided to a series of predictive models 73. The predictive models 73 can include any of appropriate supervised learning algorithms, such as regression models, artificial neural networks, support vector machines, and statistical classifiers, which may be configured to predict a likelihood of one of a plurality of disorders according to deviations between the measured biometric parameters and the baseline. In one implementation, the predictive models 73 can include an analogical reasoning algorithm that compares the patient's measured biometric parameters, genetic markers, and clinical observation by a physician to sets of biometric parameters, genetic data, and observations from other patients for whom the presence or absence of a condition is known to determine a likelihood that the patient may experience the condition. The conditions evaluated by the predictive models 73 can be drawn from one or more disorder ontologies 74. A disorder ontology can be compiled from existing resources such as the International classification of Diseases (ICD), the Diagnostic and Statistical Manual of Mental Disorders (DSM), the Medical Dictionary for Regulator Activities (MedDRA), BioOntology, and the Open Biological and Biomedical Ontologies.

It will be appreciated that the system is not limited to a rigid disorder ontology. Many pathological states are defined by symptoms, leading to imprecise classifications. For example, it is likely chronic fatigue syndrome is an umbrella class for a host of different, possibly unrelated pathologies. Other disorders, such as autism and schizophrenia, exist along a spectrum of symptom intensities, which may also group states with different underlying causes. To this end, the system can provide a complementary way to define pathologies by the underlying biological data, rather than these imprecise symptom presentations. Specifically, unique combinations of biological data (e.g., genomic, proteomic, metabolomic) will be statistically processed and associated with outcomes and symptoms to provide more precise pathological classifications. By linking the biological state directly with the pathological classification, treatments can be assigned that directly address the underlying biological cause of symptoms.

The backwards analytics performed by the system can include one or more data mining algorithms 76 that analyze data stored in the knowledge base 68 for connections between previously unconnected predictors. The connections determined from the data mining algorithms 76 can be utilized to define new causality cases for use in the forward analytics performed by the system. This process can be fully automated, with new causality cases integrated into the predictive models 73 automatically, or in a semi-supervised fashion, in which each newly discovered causality case is reviewed by a subject matter expert before being incorporated into the predictive models. The data mining algorithms 76 can include, for example, anomaly detection algorithms, association rule learning, clustering algorithms, and sequential pattern mining.

In one implementation, new causality cases are generated as treatments, protein expression changes, and outcomes and then iteratively input into the knowledge base as adjustments of any of correlations, scoring, recommendations, and weighing of causalities. This information allows researchers to evaluate hypotheses and suggests subsequent research, such as identifying new biomarkers. As the system ingests and process new data, interesting relationships will emerge as analytics and data mining algorithms are automatically run. Researchers will be able to log in and bring up an updated list of trends and statistically significant relationships that have emerged. These lists serve as an opportunity for researcher to explore the meaning behind relationships and develop hypotheses for future research projects, thereby accelerating research productivity.

The system 50 also includes an analytics component 77 configured to retrieve data from the knowledge base 68 to confirm causality cases identified by the data mining component 76 and researchers. To this end, the analytics component 77 can include integration with the Basic Local Alignment Search Tool to find commonalities between a given genetic sequence and library sequences as well as various custom analytics algorithms that automatically discover correlations between baseline protein assays and diagnosed diseases later in life, automatically discover correlations between baseline protein assays and genetic sequences, and discover new genetic markers by correlating genome with diseases or allergic reactions. Further, the analytics component 77 can include an algorithm for tracking protein level changes associated with clinical treatment outcomes to explore the biological relationship to the proteins and disease, relate to genetic mutations, and develop more effective drugs using knowledge of the causal biological interactions. Additionally, the analytics component 77 can include statistical analysis and analytic tools to assist researchers in confirming hypotheses generated by the data mining component 76 and the other analytic tools. In one implementation, the analytic tools can include advanced signal processing algorithms to extract correlations from noisy data and neural spike metrics.

Medications are often prescribed despite known side effects. The inventors have determined that the knowledge of who would be most likely to present with side effects is both within the capability of a learning healthcare information processing system 50 in accordance with an example embodiment and of considerable value, especially when alternative medications exist. Similarly, it would be possible to predict who may respond well and/or without side effects. To this end, the knowledge base 68 will be designed to collect outcome data fed back from the system 50. Positive and non-adverse outcomes may be unique for specific genetic mutations or baseline protein levels, and can therefore serve as additional information for supporting practitioner treatment recommendations and suggest areas of research and discovery. Outcomes will therefore be linked to specific genetic mutations and protein levels for individual patients to allow for prediction of patient response from proteomics and genomics.

It will be appreciated that the system may iteratively test hundreds to thousands of variables for significant correlations. While inclusion of more variables increases the probability of discovering insightful, actionable relationships, it also increases the probability of false positives. The standard approach to correct for this problem of "multiple comparisons" is to multiply significance test values by some corrective factor. For instance, in Bonferroni correction, the p value is multiplied by the number of independent tests performed. Unfortunately, this results in increasing the probability of false negatives. Therefore, the more independent significance tests run, the more interesting relationships will be buried into the background noise of non-significance.

In accordance with an aspect of an example embodiment, a rules engine 78 includes a mix of expert and machine-generated rules and weights are continuously deployed and tuned that learn which types of variables present the best probability for insightful or actionable results prior to analysis. The automated rules engine 78 is expected to supplement the efforts of expert researchers in determining what tests to run prior to a single research experiment. Reducing the overall number of tests will also optimize processing performance. Ultimately, the rules engine 78 mediates between statistical design and machine intelligence in developing healthcare-based statistical rules.

The results of the various analytics and modeling processes 70 can be provided to the knowledge base 68 to be added to the patient's record as well as any relevant medical databases 52. These records will generally be supplemented with a treatment record and a patient outcome once these factors are known. The results are also provided to respective visualization components 82-84. In one implementation, a researcher visualization component 82 presents the knowledge discovered by analytics component 77 (or analytics search engine) applied to the genetic and proteomic data collected in this system in a visual fashion that is readily comprehendible. The researcher visualization component 82 can provide a user interface for analytic search algorithms to discover correlations between protein assays, genetic sequences, and diagnoses. The researcher visualization component 82 can also include various display and graphical manipulation tools to view protein level changes associated with clinical treatment outcomes so that the researcher can explore the biological relationship to the proteins and disease, relate the outcomes and proteins to genetic mutations, and develop more effective drugs using knowledge of the causal biological interactions. The researcher visualization component 82 can also provide a periodic report of emergent statistical associations between variables across databases as outcome data is fed back into the system, as well as simply access to relevant data and findings from valuable scientific databases.

A clinician decision support component 83 allows a clinician to access results of forward analytic processes for a given patient and relevant support information. For example, the clinician decision support component 83 can display to the clinician a list of diseases consistent with the patient's clinical observations, a latest protein assay, geographic location, and relevant environmental factors in likelihood order. The clinician can also instruct the clinician decision support component 83 to display a comparison of the current protein assay with the measured or imputed baseline assay, and/or a comparison the patient's history of protein assays with the normal time series of expected protein assays. The clinician decision support component 83 can also display values significant in the calculated baseline assay, such as markers from the patient's genome and exogenous variables such as gender, weight, and age. The decision support component 83 can also notify a clinician when a patient has not been in contact with the office for a predetermined period of time or has failed to provide a scheduled biochemical assay. In one implementation, this notification can be complied over a period of time and provided in list form to avoid overwhelming the clinician.

A patient dashboard 84 can present the results of forward analytic processes and supporting data to a patient. To this end, the patient can be presented with any findings of elevated risk, the genomic, biochemical, and clinical parameters supporting the findings, and links to information related to the disorder or outcome associated with the elevated risk, potential treatments, and the parameters supporting the findings. For example, a patient could be provided with a link to information about the side effects associated with a prescribed medication. Any recommendations on health screening results and potential courses of action provided to the patient can include certainty-weighting and risk-based weighting to facilitate informed decisions by the patient. The patient dashboard 84 can also provide an interface for the patient to ask questions, via an encrypted e-mail service, such as S/MIME, to a clinician to clarify information received during an earlier visit. The patient dashboard 84 can also provide reminders to the patient for scheduled biochemical assays, appointments with clinicians, or to take or refill medicines. In one implementation, the patient can record observations of symptoms through the patient dashboard 84 as well review, correct, and supplement data in the patient's electronic medical record.

It will be appreciated that, after a medical outcome is known for a given patient, the knowledge base 68 can be updated to reflect the new result. To this end, a set of measured clinical outcomes 86 can be provided to the knowledge base 68 to augment the existing patient data. The measured clinical outcome can reflect, for example, whether the patient has a condition of interest after a set period of time after the prediction. Along with new medical research and new patient records entering the system, these patient outcomes 86 can provide the knowledge base 68 with the basis for new causality cases to be discovered by the analytics and modeling component 70.

In one example use case, a lab draws a patient's blood and provides the genomic 54 and proteomic 53 assays. In one implementation, the proteomic assay 53 can be performed using a low-cost, easily repeatable assay that can simultaneously determine levels for thousands of proteins from a small blood sample with a relatively low overhead for each testing site, allowing the test to be widely accessible. Since the test is designed to be low-cost and accessible, longitudinal data for a large population of individuals could be efficiently compiled. Once the data are normalized and processed, it can be determined if the patient's protein levels, taken in view of clinical observations of the patient, and genetic markers, indicate an enhanced likelihood of a given condition through the predictive models 73. In this example use case, it is determined that the patient has a genetic marker associated with a high risk of a particular type of cancer and elevated proteins associated with that type of cancer. The knowledge base 68 can include information indicating that a survival rate for this type of cancer is significantly higher when diagnosed within three months.

Once the enhanced risk of cancer is identified, a report is generated and the patient is notified. The patient can log into the patient dashboard 84 to view the report, which can include the diagnosis and links to information about the disorder, the proteomic and genetic data used to identify the elevated risk, and potential treatments. The report can also include a recommendation that the patient should schedule a visit with an oncologist. Similarly, a clinician associated with the patient, such as a family doctor and/or an oncologist treating the patient, can receive an alert through the clinician decision support component 83. The alert can be linked to a summary report, including an overall risk score associated with the diagnosis, the specific genetic markers and proteins relied upon for the diagnosis, with links to pertinent research, and visualization tools for viewing this data. The clinician's treatment decisions and the clinical outcome can be fed back into the knowledge base 68, along with information from follow-up visits, and comments from the patient and the clinician. These findings can then be made available to researchers, through the various tools available through the researcher visualization component 82, for further analysis.

In a second example use case, a researcher might view a summary report showing recently emergent data trends and find a high prevalence of non-adverse Pramipexole response for patients with elevated proteins associated with food allergies. The researcher could then search text within available journal articles via a text miner in the researcher visualization component 82 as well as data within the knowledge base and affiliated data sources for known relationships between a genetic mutation shared by patients who respond well to Pramipexole and the elevated protein. Assuming no known relationship is found, the researcher could develop and conduct tests to search for unidentified proteins that may also be elevated, with the hypothesis that any identified proteins might be elevated in some patients with fibromyalgia and cause increased sensitivity to allergies in patients with the genetic mutation.

The researcher can provide the results of the research and the determined hypothesis to the knowledge base and request that the proteomics lab develop an aptamer for the identified protein. Once the aptamer is generated, results from multiple patients undergoing their scheduled proteomic assays can be aggregated to confirm or refute the researcher's hypothesis. It will be appreciated that other information from the knowledge base 68 can be mined or queried to provide evidence supporting or refuting the hypothesis. Assuming that it is confirmed, further research can be performed, for example, via queries of the knowledge base 68 through the researcher visualization component 82, to find a drug that can be employed to reduce levels of this protein. This finding can then be fed back to the knowledge base 68 as a known relationship between the drug and fibromyalgia.

After all this has happened, a patient diagnosed with fibromyalgia might be determined by a clinician to be responding poorly to common medications. The clinician may wish to prescribe a dopamine agonist, but is concerned about efficacy and side effects. The clinician may instruct the patient to have blood drawn for a genomic or proteomic assay or utilize existing genomic and proteomic data from the scheduled assays for the patient. From this information, it might be determined that the patient shares the generic mutation associated with patients who respond to the dopamine agonist Pramipexole, but lacks a marker associated with patients who respond well to the dopamine agonist Ropinirole. The protein associated with increased sensitivity to allergies may also be found to be elevated in the patient. Information in the knowledge base can be automatically retrieved and provided to the clinician and the patient indicating that the protein expression level has been reduced in sixty percent of cases in which gluten has been removed from the diet.

All of this information can be provided to the clinician at the clinician decision support component 83 with a plurality of treatment options, each having an associated score representing the likelihood, generated from the predictive models 73, that the treatment will lead to a favorable clinical outcome. Two high-score treatments might include placing the patient on a gluten-free diet and prescribing Pramipexole. Accordingly, the clinician might select either option or combine the options, with the dosage of Pramipexole reduced to account for any beneficial effects of the gluten-free diet. To the extent that Pramipexole is prescribed, levels of proteins associated with the side effects can be tracked, for example, with the frequency of the patient's proteomic assays increased until the effects of the drug are clear.

The patient can also be provided with a summary report with the diagnosis, the treatment decision made by the clinician, and an appointment schedule. This report can include links to information related to diagnosis and treatment, such as online resources that describe fibromyalgia, side effects and interactions associated with the drug, and advice for pursuing a gluten-free diet. Information can also be provided for genetic markers and protein levels used in the diagnosis. The patient can use the patient dashboard 84 to record symptom levels, such as pain and fatigue, over time. Additionally, the level for the relevant proteins can be tracked over time to maintain the patient's awareness of their progress and possibly encourage compliance. The patient's reported symptoms and the clinician's observations can be fed back into the knowledge base 68 for use in evaluating the efficacy of the selected treatment and the prevalence of any side effects.

The illustrated system 50 provides a number of advantages. For example, the system enables economy of scale by testing numerous causality cases from a single blood sample. The system is capable of quantifying, aggregating, and disclosing measurement and recommendation certainty, including biosensor variability and any other potential source of error to ensure that the confidence associated with recommendations is meaningful to the patient and clinician, and the system can improve recommendation accuracy over time. As a result, the system can have sufficiently high reliability, capacity, and availability to support mission-critical use and scale with expected data increases over time, both in the available causality cases and the inclusion of new target populations.

In view of the foregoing structural and functional features described above in FIGS. 1 and 2, an example method will be better appreciated with reference to FIGS. 3 and 4. While, for purposes of simplicity of explanation, the method of FIGS. 3 and 4 are shown and described as executing serially, it is to be understood and appreciated that example embodiments are not limited by the illustrated order, as some actions could in other examples occur in different orders and/or concurrently from that shown and described herein.

FIG. 3 illustrates a method 100 for providing personalized healthcare support in accordance with an example embodiment. At 102, biochemical assays are conducted, at scheduled intervals, on a blood sample taken from an individual to provide a time series of values for each of a plurality of biochemical parameters. In one implementation, the biochemical assay is a baseline protein assay measuring a large number of protein levels from a single drop of blood, such that the assay can be low-cost and easily performed outside of a clinical environment. Accordingly, patient access to the biochemical assay can be made convenient to encourage compliance in generating a complete time series of values.

At 104, a plurality of clinical parameters, associated with the individual, from a knowledge base are extracted. The parameters can be categorical, such as diagnosed disorders or clinical observations of symptoms, as well as interval or ratio data, such as age, temperature, weight, blood pressure, cholesterol levels, and other such data. In one implementation, a plurality of cohort parameters can be extracted from respective series of biochemical assays in the knowledge base from record representing individuals who are associated with the individual. For example, the cohort parameters can include averaged time series of a given biochemical parameters across one or more of a set of people who are related to the patient, a set of people who live or work near the patient, and a set of people who share a condition or genetic marker in common with the patient.

At 106, a plurality of genomic parameters are determined for the individual. In one implementation, this can be done from the same blood sample used to derive the biochemical parameters. It will be appreciated that each of the time series of values and the plurality of genomic parameters can be stored in the knowledge base such that the knowledge base contains biochemical assays, genomic parameters, and clinical parameters for a population of patients.

Chemical and biological analysis is typically used to determine characteristic features of a biological sample. The features could then be transformed into representative quantitative values and provided to an information processing system for calculation and statistical analysis including data mining, machine learning and other computational functions. Many methods are known to those skilled in the art of biochemistry for determining signature features derived from biomedical samples and for comparing the features against other samples or across reference data sets. For example, comparing multiple mass spectra from different biological samples and identifying common features across the samples can be used as a reference condition, whereas identifying distinguishing features could serve as potential biomarkers for detection of an anomalous condition. The features can be compared across individuals and/or temporally for a specific individual. As described herein, various types of biochemical parameters are known and are available for use in analytics. Some example embodiments produce a greatly improved biochemical signature feature by combining multiple biochemical assays of different types and including a temporal component to the signature.

At 108, an expected time series is calculated for each of a plural subset of the plurality of biochemical parameters from at least the clinical parameters and the genomic parameters. For example, the expected time series can be determined as a weighted combination of time series values from patients having various characteristics associated with the clinical and genomic parameters of the patient, with the weight selected on a similarity, determined for example as a multivariate distance metric, between the patient and various other patients in the knowledge base. Alternatively, the knowledge base can be queried for patients having values for relevant biomedical parameters within a predefined range of the patient's values. The expected time series can be an unweighted average (e.g., mean or median) of the retrieved records.

In one embodiment, some example embodiments enable calculation of an expected time series by first representing the biochemical assays as feature vectors, each having a plurality of coefficients that correspond to a set of biochemical parameters. It then generates sets of clusters comprising pathological feature vectors derived from a large population of patients having a certain condition. The feature vector members of each specific cluster have signature similarities measured by a Euclidean distance calculation between the feature vector and the cluster centroid. Similarly, a well known unsupervised clustering method such as the K-means clustering algorithm can be used. Yet another alternative is to use a Mahalanobis distance for measuring similarity (correlation) with the advantage of being generally scale invariant. Furthermore, the combination of data sets and feature vectors that are associated with the biochemical assays can be represented in multiple dimensions as multivariate vectors or matrices and the clustering and distance calculations can be performed by fusing and correlating the multivariate vectors or matrices across the biochemical assay feature vector sets. There are many more distance measures and feature vector types that are known to those skilled in the art of statistical analysis. The embodiment described herein is shown only by way of example and it is understood that various alternatives can be used without a loss of generality.

The temporal aspect is now introduced where the sequences of cluster centroids are tracked over time and characterized by a cluster transition path. The time series value of an individual patient's biochemical assays can be compared to the expected time series by computing the distances of the associated feature vectors to the nearest-neighbor clusters, as each new blood sample is taken (e.g. on an annual basis). As an enhancement to the calculation, unnecessary features that are abundant in large bioinformatics data sets, and that do not materially contribute to system outcome/value, can be removed, thereby improving the results. Many other methods are available for performing supervised machine learning and data mining that are well known to those skilled in the art of data analysis.

At 110, for each of the plural subset of biochemical parameters, the time series of values representing the individual is compared to the calculated expected time series to determine a likelihood of each of a plurality of conditions for the individual. For example, a significant deviation of the time series of values from the calculated expected time series can be determined and applied as an input to a predictive model associated with one of the plurality of conditions, with the predictive model being configured to determine the likelihood of the associated one of the plurality of conditions from at least one parameter derived from the significant deviation. In one implementation, predictive models can be generated and refined by unsupervised learning processes mediated by subject matter experts. For example, a data mining algorithm can be applied to the knowledge base to identify at least one causality case relating one of the clinical parameters, the genomic parameters, and the cohort parameters to a condition. Once the causality case has been reviewed and verified by subject matter experts, for example, via the application of one or more analytic tools to retrieve evidence from the knowledge base, a predictive model can be refined or generated according to the identified causality case.

At 112, the likelihood of at least one of the plurality of conditions is communicated to a user. In one implementation, the user is the individual and the communication can include any or all of a healthcare treatment course of action, based on the communicated likelihood of the at least one condition, an instruction to the individual when a next biochemical assay should be scheduled based on the communicated likelihood of the at least one condition, and a recommendation as to a type of healthcare practitioner from which the individual should seek treatment. In another implementation, the user is a clinician and the communication includes a recommended protocol of care to the clinician based on the communicated likelihood of the at least one condition.

In one implementation, the communication is provided through a user interface that is configured to display to the user, for a selected one of the plural subset of biochemical parameters, a graphical representation of each of the time series representing the individual for the selected biochemical parameter and the calculated expected time series for the selected biochemical parameter, such that the calculated expected time series can be easily compared to measured values from the scheduled biochemical assays. The user interface can allow a clinician to select a new value from a selected one of the parameters used to calculate the expected time series and alter the graphical representation of the expected time series to reflect the new value of the selected parameter. This can allow the clinician to determine the effects of possible treatments and lifestyle modifications on a patient's health. It will further be appreciated that these tools can be made available to researchers for assistance in searching for new causality cases.

FIG. 4 illustrates a method 150 for discovering and applying new causality cases in a learning healthcare system in accordance with an aspect of an example embodiment. At 152, a knowledge base associated with the learning healthcare system can be updated with measured clinical outcomes for patients in the knowledge base. For example, the measured outcomes can be entered directly into the system via a user interface or retrieved from a medical records database. At 154, unsupervised learning processes are performed on the knowledge base to discover potential causality cases. The unsupervised learning processes can include, for example, anomaly detection algorithms, association rule learning, clustering algorithms, and sequential pattern mining.

At 156, an analyst is prompted to perform one or more analytics on the knowledge base to confirm a potential causality case. For example, a researcher might be provided with a summary report showing recently emergent data trends, with the appropriate supporting data available for review as text or a graphical representation. The researcher could then search text within available journal articles via a text miner or formulate one or more queries of related data in the knowledge base to develop a hypothesis for any emergent trends found to be of interest. The researcher could then develop and conduct tests to confirm the hypothesis, with the results of the research and the determined hypothesis provided to the knowledge base. If the hypothesis representing the causality case is confirmed, one or more predictive models are updated at 158 to reflect the new finding.

FIG. 5 is a schematic block diagram illustrating an exemplary system 200 of hardware components capable of implementing examples of the systems and methods disclosed in FIGS. 1-4, such as the learning health system illustrated in FIGS. 1 and 2. The system 200 can include various systems and subsystems. The system 200 can be a personal computer, a laptop computer, a mobile device, a tablet computer, a workstation, a computer system, an appliance, an application-specific integrated circuit (ASIC), a server, a server blade center, a server farm, etc.

The system 200 can include a system bus 202, a processing unit 204, a system memory 206, memory devices 208 and 210, a communication interface 212 (e.g., a network interface), a communication link 214, a display 216 (e.g., a video screen), and an input device 218 (e.g., a keyboard and/or a mouse). The system bus 202 can be in communication with the processing unit 204 and the system memory 206. The additional memory devices 208 and 210, such as a hard disk drive, server, stand alone database, or other non-volatile memory, can also be in communication with the system bus 202. The system bus 202 interconnects the processing unit 204, the memory devices 206-210, the communication interface 212, the display 216, and the input device 218. In some examples, the system bus 202 also interconnects an additional port (not shown), such as a universal serial bus (USB) port.

The processing unit 204 can be a computing device and can include an application-specific integrated circuit (ASIC). The processing unit 204 executes a set of instructions to implement the operations of examples disclosed herein. The processing unit can include a processing core. Although one processing unit 204 is shown in FIG. 5, it should be appreciated that the processing unit 204 may be distributed in some examples. Thus, for example, multiple instances of processing circuitry may be embodied at a plurality of different locations within an enterprise or within a network and the various instances of processing circuitry may communicate and combine their respective processing capabilities to embody the processing unit 204 of the system 200. Similarly, other components of FIG. 5 should also be appreciated to have the potential for multiplicity and distribution in various different example implementations.

The additional memory devices 206, 208 and 210 can store data, programs, instructions, database queries in text or compiled form, and any other information that can be needed to operate a computer. The memories 206, 208 and 210 can be implemented as computer-readable media (integrated or removable) such as a memory card, disk drive, compact disk (CD), or server accessible over a network. In certain examples, the memories 206, 208 and 210 can comprise text, images, video, and/or audio, portions of which can be available in formats comprehensible to human beings.

Additionally or alternatively, the system 200 can access an external data source or query source through the communication interface 212, which can communicate with the system bus 202 and the communication link 214.

In operation, the system 200 can be used to implement one or more parts of a learning health system in accordance with an example embodiment. Computer executable logic for implementing the composite applications testing system resides on one or more of the system memory 206, and the memory devices 208, 210 in accordance with certain examples. The processing unit 204 executes one or more computer executable instructions originating from the system memory 206 and the memory devices 208 and 210. The term "computer readable medium" as used herein refers to a medium that participates in providing instructions to the processing unit 204 for execution.

As discussed above, the system 200 may be configured to implement the methods and systems of FIGS. 1-4, which generally may incorporate genomic data and proteomic data to improve healthcare outcomes. However, some example embodiments may also achieve improved healthcare outcomes using clinical data, genomic data and other relevant types of data. The clinical data may include patient health record information (e.g., electronic health record (EHR) information) and laboratory data. However, laboratory data may be considered to be distinct from clinical data in some cases since, for example, the laboratory data may have a different format (e.g., pdf) within an EHR. The genomic data may include sequenced genomes of patients. The other relevant types of data may include, for example, research data, and text or publication data from various biomedical literature sources (e.g., PubMed sources). Thus, for example, the system 200 may be configured to generate a personalized healthcare and informatics system that can use genetic data to drive healthcare outcome improvements. Other supplemental information may also be added. However, in accordance with this example embodiment, sizable gains in healthcare outcome improvement can be obtained by employing heterogeneous data sources that include genomic data, and then employing powerful analytic tools and visualization tools to improve patient healthcare and status.

In some embodiments, the system 200 may be employed to embody a closed feedback loop architecture for providing the data, analytics, modeling and interface capabilities to enable association of multiple data sources to provide insight into patient health risks and conditions, while also enabling the data sources to be dynamically updated and further used to support further research. The closed loop feedback architecture may be mainly constructed using open source components. However, proprietary solutions may be substituted for some components where desired. The analytic capabilities of the system 200 may be employed to associate clinical, genomic and proteomic biomarkers to patient health record data to provide the insight. In particular, the system 200 may provide massive amounts of genomics data that includes patient de-identified (e.g., by removing the identities of the individuals with which such data is associated) genomic data and identified genomic data along with identified and de-identified clinical data to be stored and analyzed to enable further research and healthcare decision support to be conducted using cloud based and scalable resources. The system 200 is dynamic, and thus is configured to discover and update clinical, genomic and/or proteomic interpretations and algorithms continuously. As discussed above, the data associated with the system 200 can be compared against clinical outcomes. Some embodiments may further provide a user interface to deliver visualizations of customized results or responses to queries to patients, physicians, and researchers to identify and diagnose emerging diseases and guide treatment interventions.

In an example embodiment, the architecture that the system 200 embodies or supports may have multiple layers including a storage/data layer, an analytics layer and an application layer supported on a cloud-based platform. A block diagram of such a platform is shown, for example, in FIG. 6. As shown in FIG. 6, a data platform 300 may be provided to support or embody the storage/data layer. Because the storage/data layer may include data of various different types and structures, the data platform 300 may include a broad variety of databases to support various different storage and retrieval mechanisms for corresponding different data types and structures. For example, the data platform 300 may include a relational database management system (RDBMS) 302 that is based on a relational database model. The data platform 300 may also include a NoSQL database 304 to provide a mechanism for storage and retrieval of data that is modeled in means other than tabular relations used in relational databases. In some cases, the data platform 300 may include a Hadoop component 306, which may provide an open-source framework for distributed storage and processing of very large data sets on computer clusters. The Hadoop component 306 may be particularly useful in supporting "big data" analytics on genome data and/or proteomics data. In an example embodiment, the Hadoop component 306 may be supplemented with or replaced by Google Genomics for storage of massive amounts of genomic data. In some embodiments, the data platform 300 may include a Greenplum database or other analytics database 308, and one or more composite data virtualization components and/or business intelligence and analytics platform (e.g., BI platform 310) or other data integration platforms (e.g., Pentaho and/or SAS Access). Thus, it should be appreciated that the data platform 300 can support multiple types and structures of data and mechanisms for accessing such data. The data platform 300 can therefore be a scalable platform to provide data sources including structured and unstructured data that can be analyzed using an analytics platform 320 that may support or embody the analytics layer. The data may include patient health record information (e.g., EHR information), research data, genomic data (e.g., patients' sequenced genomes), and text or publication data from various biomedical literature sources (e.g., PubMed sources).

The analytics platform 320 may include analytics tools configured to interface with the various different data sources. Because the data sources are so diverse, the analytics tools must be equally diverse to be able to analyze the data and make correlations where appropriate. Moreover, the correlations to be made in the context of such massive amounts of data need to be made relative to user input (e.g., a query) in the form of a response that can be provided in real-time or near real-time. Thus, the analytics platform 320 provides analytical tools to respond to user queries by analyzing large and diverse data sets relative to a particular condition or medical issue to identify relevant correlations and/or patterns in the data based on the query received. Once the relevant correlations and/or patterns are identified, they can be processed according to human-defined and/or machine learned rules corresponding to risk models defined for various conditions or relative to certain issues. Thus, the analytics platform 320 is configured to perform fast analytics on massive amounts of data (e.g., multiple terabytes of data) to provide specific decision support responses that are germane to the queries provided.

The analytics platform 320 of an example embodiment may include at least a statistical discovery component 322 (e.g., SAS analytics and/or JMP, or a component designed using R (i.e., an open-source programming language for statistical computation)) and a natural language processing component (e.g., NLP engine 324). The statistical discovery component 322 may be configured to interface with portions of the data sources that include structured data (e.g., some EHR data, some research data, genomic data, etc.) to selectively identify correlations based on analysis of contents of the data sources and the query defined by the user. The NLP engine 324 may be configured to interface with portions of the data sources that include unstructured data (e.g., some EHR data, some research data, clinical data and publications, etc.) to selectively identify correlations based on analysis of contents of the data sources and the query defined by the user.

The analytics platform 320 may interface with a modeling component 330 configured to apply a selected risk model based on the query. The risk models may be any of a plurality of health models associated with different diseases, health issues or health conditions (e.g., cancer, heart disease, mental health, diabetes, pathogen detection, prescription drug therapy, arthritis, etc.). The modeling component 330 may include a rules engine 332 and/or one or more algorithm implementers (e.g., Bayes Net or components designed using R) 334 that provide risk models to which the analytics platform 320 output can be compared to place correlations and/or patterns identified in the data sources into a meaningful context relative to the query. The rules engine 332 may employ Drools to process rules.

The modeling component 330 may interface with a user interface component 340, which may be provided at the application layer, and which may be configured to enable a user to provide the query 350, and to generate a response 360 to the query 350. The response 360 may provide information associated with clinical decision support that is tailored to an identity (or role) of the user. Thus, for example, the same system can support access by multiple different types of users (e.g., patients, clinicians and researchers) to provide useful and potentially different levels of access and information extraction from the same massive repository of data to support various applications such as research, clinical trials, drug discovery and patient care. To this end, the infrastructure of the system 200 may further employ a data security and access component 370. The data security and access component 370 may ensure that any information access restrictions that are appropriate for respective different data sources are enforced.

Some example embodiments may provide strong capabilities for a closed feedback loop for employment of specific analytics tools to discover correlations within data being analyzed based on the queries provided by the user. FIG. 7 illustrates a block diagram of the mechanisms and platforms associated with practicing example embodiments. As shown in FIG. 7, various data sources 400 (e.g., genomic data, health record data, clinical research data, PubMed texts and publications, etc.) may be accessed to find correlations and/or patterns at operation 410. The correlations may be found by machine learning 412 or by human intervention 414. These correlations may be used to generate rules at operation 420. Again, the generation may be guided or performed via machine learning 422 or by human intervention 424. Thereafter, rules engines or algorithm implementors may operate at operation 430 to drive decision support responses based on queries received at operation 440.

Example embodiments may be employed for analysis of genomic and/or clinical risk based on the genome data and/or clinical data as a portion of the data sources 400. In this regard, there is over a terabyte of genomic data that is available for analysis and example embodiments may integrate the genomic data with patient health record data including genomic markers of specific patients to identify, by employing corresponding risk models for specific medical conditions or diseases, a risk score for the patient relative to a likelihood of having the corresponding medical condition or disease for which a query is received. Accordingly, the data sources 400 may be analyzed to identify a selected risk model based on a query and generate a response to indicate a degree of risk of the patient having a condition associated with the selected risk model. The selected risk model may be selected based at least in part on the genetic markers and clinical parameters of the patient and selected portions of the genetic data. The selected portions of the genetic data may be considered to be reference genetic data that is pertinent to the query (e.g., to the condition or disease of interest for a particular patient). As such, individual clinical data and genomic data (e.g., including genetic biomarkers) of the patient can be used along with identification of a specific disease, condition, drug or other query, to identify risks for the patient based at least in part on reference genetic data (and perhaps also reference clinical data) selected from among the massive amounts of patient de-identified data in the data sources 400.

Thus, for example, the patient or a clinician may access a record associated with the patient. A query may be provided to request a risk score for a specific type of cancer. The risk score would then be the response to the query. The system 200 may access (among other things) information associated with the patient's genomic markers that are pertinent to risk for the specific type of cancer and the massive amounts of genomic data relating to other patients having and not having the corresponding specific type of cancer. Based on the pertinent information extracted from the analytics platform 320 and application of the modeling component 330, a risk score may be calculated for the patient based on the correspondence between the genetic profile of the patient and genetic biomarkers associated with the genomic data of others having the cancer. In some cases, the risk score may be a composite risk score that further considers proteomic data, clinical data and/or the like. However, the data platform 300, the analytics platform 320 and the modeling platform 330 may each be dynamically updateable. Thus, risk scores, models, profiles of various types and various other aspects of the system may be updateable to allow updated processing and decision support to be performed over time. Moreover, additional modules with different types of data sources and corresponding risk models can also be added to the scalable system provided by example embodiments.

In an example embodiment, the query may include identifying information indicative of a drug prescribed or in consideration for being prescribed for the patient. In such an example, the response to the query may include a risk score relative to the likelihood of one or more complications being experienced by the patient. Alternatively or additionally, the response may include an indication of drug variants and risks relative to a drug of interest (i.e., the drug prescribed) based on a pharmacogenomic profile generated for the patient based on gene variance analysis. Thus, the analytic platform 320 and the modeling component 330 may interact to identify, based on the genetic profile of the patient, a specific drug alternative that may be less likely to cause undesirable side effects for the patient. Alternatively or additionally, the information on drug variants may be directed to providing positive side effects instead of the avoidance of negative side effects. In this regard, the pharmocogenomic profile of the patient, coupled with genetic data from many other patients with data indicating positive results or benefits of employing a particular drug or treatment regimen may be matched by the system to provide data that can be useful to a clinician in making healthcare decisions for the patient.

Ultimately, example embodiments enable heterogeneous data from a plurality of sources with different formats to be stored and analyzed from a single scalable system. Analytics, some of which is tailored specifically to the different types/structures of data in the data sources, may then be applied in real time by users that may have distinctly different uses for the information and desired outputs based on a query provided by a particular one of the users. Responsive to the query, the analytics may identify pertinent information and apply rules/models that are applicable to generate a response in the form of a useful visualization for the user. Thus, different types of users can get different types of responses out of the same data set and using the same system. However, the system can tailor the responses to the user by providing visualization tools and techniques that are tailored to the users. Essentially, the system packages information (e.g., genetic information and/or the like) into a form that can make it usable to support clinical decision making and information dissemination. The system can also be useful to process genetic information for different purposes such as finding drug variants or disease variants that are likely to impact a particular patient. Thus, the impact of a drug or disease on a patient may be studied on the basis of the genetic profile of the patient.

The provision of a scalable system for analyzing data of different types from a plurality of different sources for use by patients, clinicians and researchers can provide a flexible platform for the improvement of healthcare solutions for individual patients in the manner described above. However, such a platform may also allow, by virtue of its scalable nature, various specifically programmed modules to be plugged into the system 200 to enable additional specific functions to be performed relative to the various types of data that are made accessible to analytical tools via the system 200. In an example embodiment, the system 200 may be augmented with a drug discovery module 500 shown in FIG. 8. The drug discovery module 500 may be a module that is executable in any environment (e.g., a cloud environment or locally on a server, laptop or computer terminal). In this context, the term "module" should not be understood as a nonce word to identify any generic means for performing functionalities of the drug discovery module 500. Instead, the term "module" should be understood to be a modular component that can be added to the existing system 200 to modify the behavior and/or capability of the system 200 based on the hardware and/or software added to the system 200 to embody the drug discovery module 500. Although modular, it should also be appreciated that some code portions of the drug discovery module 500 may be shared by other modules or components.

The drug discovery module 500 may include processing circuitry 510 of an example embodiment as described herein. In this regard, for example, the drug discovery module 500 may utilize the processing circuitry 510 to provide electronic control inputs to one or more functional units of the drug discovery module 500 to obtain and/or process data associated with the one or more functional units and perform the drug discovery processes described herein. In particular, the drug discovery module 500 may be configured to identify (or discover) potential drugs for treatment of diseases based on identifying links between drugs and biomarkers and corresponding links between biomarkers and diseases. To accomplish the linkages described above, the drug discovery module 500 may further include a pharmaco-genomic mapper 550 and a genome connect module 560 as described herein. The pharmaco-genomic mapper 550 may provide a mapping of drugs to biomarkers, and the genome connect module 560 may provide a mapping of biomarkers to diseases. Thus, by correlating the two mappings together, the drug discovery module 500 may be configured to ultimately link drugs to diseases to provide potential correlations between drugs and diseases that can later form the basis of drug trials to confirm whether such correlations are valid.

In some embodiments, the processing circuitry 510 may be embodied as a chip or chip set. In other words, the processing circuitry 510 may comprise one or more physical packages (e.g., chips) including materials, components and/or wires on a structural assembly (e.g., a baseboard). The structural assembly may provide physical strength, conservation of size, and/or limitation of electrical interaction for component circuitry included thereon. The processing circuitry 510 may therefore, in some cases, be configured to implement an embodiment of the present invention on a single chip or as a single "system on a chip." As such, in some cases, a chip or chipset may constitute means for performing one or more operations for providing the functionalities described herein.

In an example embodiment, the processing circuitry 510 may include one or more instances of a processor 512 and memory 514 that may be in communication with or otherwise control a device interface 520 and, in some cases, a user interface 530. As such, the processing circuitry 510 may be embodied as a circuit chip (e.g., an integrated circuit chip) configured (e.g., with hardware or a combination of hardware and software) to perform operations described herein. Thus, in some embodiments, the processing circuitry 510 may be embodied as a portion of a computer terminal or a hand held communication device of the system 200.

The user interface 530 may be in communication with the processing circuitry 510 to receive an indication of a user input at the user interface 530 and/or to provide an audible, visual, tactile or other output to the user. As such, the user interface 530 may include, for example, a display, one or more switches, buttons or keys (e.g., a keyboard or other function buttons), a mouse, and/or other input/output mechanisms. In an example embodiment, the user interface 530 may include one or a plurality of lights, a display, a speaker, a microphone, and/or the like. In some embodiments, the user interface 530 may also provide interface mechanisms that are generated on the display for facilitating user interaction. Thus, for example, the user interface 530 may be configured to provide interface consoles, web pages, web portals, drop down menus, buttons, and/or the like, and components thereof to facilitate user interaction.

The device interface 520 may include one or more interface mechanisms for enabling communication with other devices (e.g., servers, external network communication devices, etc.). In some cases, the device interface 520 may be any means such as a device or circuitry embodied in either hardware, or a combination of hardware and software that is configured to receive and/or transmit data from/to devices or components in communication with the processing circuitry 510 via internal and/or external communication mechanisms. In some cases, the device interface 520 may further include wired and/or wireless communication equipment (e.g., one or more antennas) for at least communicating with the servers or computers of a network such as the Internet. As such, in some cases, the device interface 520 may enable the drug discovery module 500 to communicate with other devices "in the cloud." However, in some cases, the drug discovery module 500 may actually be a cloud component and the device interface 520 may allow the drug discovery module 500 to communicate with the other devices or components from the cloud in such examples.

The processor 512 may be embodied in a number of different ways. For example, the processor 512 may be embodied as various processing means such as one or more of a microprocessor or other processing element, a coprocessor, a controller or various other computing or processing devices including integrated circuits such as, for example, an ASIC (application specific integrated circuit), an FPGA (field programmable gate array), or the like. In an example embodiment, the processor 512 may be configured to execute instructions stored in the memory 514 or otherwise accessible to the processor 512. As such, whether configured by hardware or by a combination of hardware and software, the processor 512 may represent an entity (e.g., physically embodied in circuitry—in the form of processing circuitry 510) capable of performing operations according to embodiments of the present invention while configured accordingly. Thus, for example, when the processor 512 is embodied as an ASIC, FPGA or the like, the processor 512 may be specifically configured hardware for conducting the operations described herein. Alternatively, as another example, when the processor 512 is embodied as an executor of software instructions, the instructions may specifically configure the processor 512 to perform the operations and algorithms described herein.

In an example embodiment, the processor 512 (or the processing circuitry 510) may be embodied as, include or otherwise control the operation of the drug discovery module 500 based on inputs received by the processing circuitry 510. As such, in some embodiments, the processor 512 (or the processing circuitry 510) may be said to cause each of the operations described in connection with the drug discovery module 500 in relation to operation of the drug discovery module 500 relative to undertaking the corresponding functionalities associated therewith responsive to execution of instructions or algorithms configuring the processor 512 (or processing circuitry 510) accordingly.

In an example embodiment, the memory 514 may include one or more non-transitory memory devices such as, for example, volatile and/or non-volatile memory that may be either fixed or removable. The memory 514 may be configured to store information, data, applications, instructions or the like for enabling the processing circuitry 510 to carry out various functions in accordance with exemplary embodiments of the present invention. For example, the memory 514 could be configured to buffer input data for processing by the processor 512. Additionally or alternatively, the memory 514 could be configured to store instructions for execution by the processor 512. As yet another alternative or additional capability, the memory 514 may include one or more databases that may store a variety of data sets responsive to or to facilitate operation of the drug discovery module 500. Among the contents of the memory 514, applications may be stored for execution by the processor 512 in order to carry out the functionality associated with each respective application. In some cases, the applications may include instructions for carrying out some or all of the operations described in reference to the algorithm of FIG. 9.

As mentioned above, the drug discovery module 500 may be configured to determine potential correlations between drugs and diseases by bridging two separate mappings using the pharmaco-genomic mapper 550 and the genome connect module 560. In an example embodiment, the pharmaco-genomic mapper 550 may be any means such as a device or circuitry embodied in either hardware, or a combination of hardware and software that is configured to provide a mapping between drugs and biomarkers. The mapping between drugs and biomarkers may be formed by extracting correlations between drugs and biomarkers from drug trial data and, in some cases, perhaps other sources as well. Of note, at least some of the data used to form the mapping includes not matched data (i.e., data regarding biomarkers produced by drugs in a drug trial where the biomarkers did not match desired results for the condition or disease being studied from a drug trial).

An important consideration relative to the use of biomarkers is the fact that different types or classifications of biomarkers may exist. Moreover, the reliability of biomarkers as indicators or reflectors of the mechanism sought to be measured may also be variable or in question in various different contexts. Furthermore, some biomarkers may be significant indicators only when in the presence of other biomarkers as part of a combination of biomarkers. Thus, correlations between biomarkers and clinical efficacy or toxicity are, in many cases, not perfectly accurate. Instead, the biomarkers can be useful indicators for recognition of patterns or possible correlations to a certain degree of statistical certainty, but further validation and confirmation is often conducted when a possible correlation appears to emerge.

As stated above, example embodiments may employ data that would otherwise be discarded from clinical trials since no match for the disease of interest was found. Although no match for the disease of interest is found, biomarker to drug correlations may still be indicated within or inferred from the clinical trial data. However, such correlations may, for example, have less rigorous validation performed on them relative to the correlations made for drugs that are ultimately selected from the clinical trial for treatment of a disease. Thus, in an example embodiment, the pharmaco-genomic mapper 550 may be configured to generate a mapping of potential links based on data upon which varying levels of rigorous study or validation is applicable. To account for this, the pharmaco-genomic mapper 550 may be configured to apply a mapping score to potential correlations that are evident from the data extracted and analyzed. The mapping score may be required to be above a particular threshold before any potential link may be established for mapping purposes. In some cases, once the threshold mapping score is achieved, the link may be considered to be established, and may be stored or otherwise provided in a list of links that can be compared against each other or provided to other modules for consideration or aggregation.

In some cases, the mapping score may be generated based on some indicator of data quantity and/or quality. Links that are supported by large studies (e.g., studies having a large dataset) or by a large amount of smaller studies may be considered to be stronger based on the quantity of data providing a greater statistical likelihood that confidence can be placed in such links. Thus, in some cases, the mapping score may include a quantity score component. Likewise, links having an indication of a strong validation may be considered to be of higher quality than links having a weaker indication of validation. Thus, strength of validation or an indication of the general acceptance of a particular study or data set may cause certain links to be given a high quality score. In some cases, data extracted to support a potential link may be weighted based on quality and/or quantity scores and aggregated to develop the mapping score.

In an example embodiment, the quality score may be based at least in part on a subjective ranking of the data source. In this regard, particularly in the world of big data, even weak indicators, when such indicators show up with a high frequency, may be considered to be significant. Thus, for support of big data analytics that are achievable via the system 200 described herein, and via the drug discover module 500 in particular, even data associated with unmatched drug and biomarker candidates from a particular study may have statistically valuable information associated therewith. The pharmaco-genomic mapper 550 of an example embodiment, employs even this otherwise discarded data (albeit potentially with a weighting factor that could, in some cases, disadvantage such data) to consider potential drug to biomarker mappings that could help point researchers to possible links between drugs and diseases that should be investigated.

In an example embodiment, the pharmaco-genomic mapper 550 may include or be in communication with a scoring module 552 to generate the mapping score responsive to or in connection with data extraction and modeling performed by an analytics and modeling unit 554 (e.g., from the analytic platform 320 and the modeling component 330) configured specifically for analyzing extracted data and for employing models generated specifically to identify potential drug to biomarker links. The models may be proprietary or may be publically available models that can be employed in the pharmaco-genomic mapper 550. As such, for example, the operator may insert new models or analytical tools as such models/tools are developed. Moreover, in some cases, the operator may be enabled to alter the weighting factors provided in the scoring module 552 based on experience or experimentation to alter the calculations performed when scoring algorithms are in operation to generate the mapping score or the links themselves. The scoring module 552 may, in some cases, provide a score based on the data sources and/or may provide a score based on results of analytics and modeling having been run on data extracted from the data sources.

The genome connect module 560 may be configured to provide a mapping of biomarkers to diseases. The mappings or potential links that are generated by the genome connect module 560 may similarly be generated based on extracting data potentially indicative of such links and running analytics and modeling to generate potential links. The potential links may also be scored in a similar manner (e.g., by a scoring module 562) to that described above for the drug to biomarker mapping scores.

The scoring module 562 may generate the mapping score responsive to or in connection with data extraction and modeling performed by an analytics and modeling unit 564 (e.g., from the analytic platform 320 and the modeling component 330) configured specifically for analyzing extracted data and for employing models generated specifically to identify potential biomarker to disease links. The scoring module 562 may, in some cases, provide a score based on the data sources and/or may provide a score based on results of analytics and modeling having been run on data extracted from the data sources.

The analytics and modeling unit 564 may be configured to employ proprietary or publically available models to extract links or potential links from the data sources accessed, and if such potential links have mapping scores greater than a threshold score, the links may be established for mapping purposes. In some cases, a plurality of biomarkers (e.g., on the order of hundreds or even thousands) may be associated with a particular disease in some way. However, of the large plurality of biomarkers, perhaps a small subset may be thought to have a strong correlation, and some may only have a strong correlation in the presence of other particular biomarkers. Thus, the correlations between biomarkers and the particular disease may be scored based on the strength of correlation or based on the presence or absence of other biomarkers that form combinations having significance.

In an example embodiment, the mapping score of the pharmaco-genomic mapper 550 and the mapping score of the genome connect module 560 may be combined or otherwise employed to define a potential drug to disease link using the biomarkers as a bridge. In some cases, the potential drug to disease link may be associated with a composite mapping score or a link score by the drug discovery module 500. Composite mapping scores above a composite threshold may, for example, be provided in a list of potential drug to disease links that can be organized by drug, by disease, or by other bioscience data terms or variables that can be entered by the operator as a query. Thus, for example, the operator may select a particular drug and see a list of potentially linked diseases for the particular drug. In some cases, these links can be displayed (e.g., via the user interface 530) along with their respective mapping scores (including the components thereof or as the composite score) in rank order, alphabetical order, and/or the like. An operator may then appreciate the strongest possible links and endeavor to further study or validate such links. Similarly, the operator may select a particular disease and see a list of potentially linked drugs for the particular disease again by rank, alphabetical or some other order. The scores and components thereof may be provided and, in some cases, selectable to retrieve details about the biomarkers, the scoring algorithms used, the data sources, and/or other information associated with formation of the corresponding links.

In an example embodiment, the mappings may be used by the drug discovery module 500 to identify correlations (i.e., bridging links) that are direct links (e.g., a one-to-one association) or indirect links (e.g., not one-to-one associations. For example, a direct link may make an association between drug A and disease B via a single biomarker x1. In this regard, a first study may identify a link between drug A and biomarker x1. In some cases, the link may be identified by virtue of a mapping score having above a threshold level. However, the link may be identified in other ways as well. Meanwhile, another study may identify a link between biomarker x1 and disease B. Thus, the drug discovery module 500 may be configured to identify a direct link from drug A to disease B via biomarker x1 based on a one-to-one correlation of the outputs from the pharmaco-genomic mapper 550 and the genome connect module 560.

However, for establishment of an indirect link, the drug discovery module 500 may be configured to employ an understanding of biomarker pathways to form the indirect links. As an example, an indirect link may make an association between drug A and disease B via two different biomarkers (e.g., biomarker x1 and biomarker x2) that are linked via biopathways. In this regard, a first study may identify a link between drug A and biomarker x1. Another study may identify a link between biomarker x2 and disease B. Still another study may identify an association between biomarker x1 and biomarker x2 that suggests a possible biopathway link between the biomarkers. Thus, the drug discovery module 500 may be configured to identify an indirect link from drug A to disease B via biomarker x1 and its biomarker pathway-linked biomarker x2 based on a correlation of the outputs from the pharmaco-genomic mapper 550 and the genome connect module 560 that is not a one-to-one correlation. As can be appreciated from this example, the drug discovery module 500 may be configured to extract information suggestive of biopathway links between biomarkers in literature or in data to find the associations that support the creation of the indirect links.

As such, as mentioned above, the drug discovery module 500 may be configured to determine potential correlations between drugs and diseases by bridging the mappings provided by the pharmaco-genomic mapper 550 and the genome connect module 560 in which at least some of the data used to form the mapping includes not matched data from drug trials.

FIG. 9 illustrates a block diagram of operations associated with an example algorithm for facilitating drug discovery in accordance with an example embodiment. Of note, the method or algorithm shown in FIG. 9 is merely one example of how components of one example embodiment may operate, and thus FIG. 9 is not intended to be limiting. Other example embodiments may add steps, omit steps, or employ different steps in some cases. The method may include receiving a query at operation 600. A determination may then be made, at operation 610, as to whether the query is in relation to a drug, a biomarker or a disease. If the query identifies a drug of interest, mappings may be acquired for connections between the drug of interest and biomarkers that were associated therewith in clinical trial data at operation 620. If the query identifies a disease (or condition) of interest, mappings may be acquired for connections between the disease (or condition) of interest and biomarkers that were associated therewith in clinical trial data at operation 630. A determination may then be made at operation 640 as to whether any bridging or linking biomarkers exist to link the biomarkers identified in operation 620 to diseases or link the biomarkers identified in operation 630 to drugs. At operation 650, a list may be determined of links for the query that proceed from drug to disease through linking biomarkers. If the determination at operation 610 indicates that the query was a biomarker, then mappings from drug to biomarker and biomarker to disease may be correlated via bridging or linking biomarkers at operation 660. Thereafter, a list of links including the biomarker and having a path from drug to disease through the biomarker may be determined at operation 670. The lists generated by operations 650 and 670 may, in some cases, be scored to determine if the composite scores of links therein are above a threshold at operation 680. Those potential drug to disease links that have qualifying scores may then be generated into a list at operation 690.

FIG. 10 illustrates a method of providing drug discovery in accordance with an example embodiment. As shown in FIG. 10, the method may include accessing information associated with genetic markers from a data platform scalable to include a plurality of data sources at operation 700. The data sources may include at least a clinical research database providing results of clinical trials. The method may further include employing a drug discovery module to provide a mapping of drugs to biomarkers based on the information at operation 710, and employing the drug discovery module to provide a mapping of biomarkers to diseases based on the information at operation 720. The drug discovery module may include processing circuitry configured to provide a potential drug to disease link based on the mapping of drugs to biomarkers and the mapping of biomarkers to diseases using the biomarkers as a bridge between the respective mappings.

In an example embodiment, an apparatus for performing the methods of FIGS. 9 and 10 above may comprise a processor or processing circuitry configured to perform some or each of the operations (600-720) described above. The processor (e.g., processing unit 204 or processor 512) may, for example, be configured to perform the operations (600-720) by performing hardware implemented logical functions, executing stored instructions, or executing algorithms for performing each of the operations.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

What is claimed is:

1. A drug discovery system, the system comprising:
a data platform scalable to include a plurality of data sources, the data sources including at least a clinical research database providing matched data and not matched data from results of clinical trials;
a drug discovery module comprising a pharmaco-genomic mapper configured to analyze terabytes of data from the data sources to:
evaluate the matched data to define a mapping of drugs to biomarkers determined based on a first qualitative and quantitative assessment to have a first mapping score above a first threshold, and
evaluate the not matched data to include at least some of the not matched data within the mapping of drugs to biomarkers determined based on the first qualitative and quantitative assessment to have the first mapping score above the first threshold; and
a genome connect module configured to:
evaluate the matched data to define a mapping of biomarkers to diseases determined based on a second qualitative and quantitative assessment to have a second mapping score above a second threshold, and
evaluate the not matched data to include at least some of the not matched data within the mapping of biomarkers to diseases determined based on the second qualitative and quantitative assessment to have the second mapping score above the second threshold,
the drug discovery module comprising processing circuitry configured to provide a potential drug to disease link based on the mapping of drugs to biomarkers and the mapping of biomarkers to diseases using the biomarkers as a bridge between respective mappings,
wherein the first and second mapping scores indicate a level of validation for each respective mapping.

2. The system of claim 1, further comprising a user interface component configured to enable a user to provide a query, and to generate a response to the query, the response providing the potential drug to disease link.

3. The system of claim 2, wherein the query defines a drug, a disease or a biomarker, and wherein the response defines a list of potential drug to disease links including the drug, the disease or the biomarker.

4. The system of claim 3, wherein the list is defined based on the potential drug to disease links that have a composite mapping score greater than a predefined threshold.

5. The system of claim 4, wherein the composite mapping score comprises the first mapping score for the mapping of drugs to biomarkers and the second mapping score for the mapping of biomarkers to diseases.

6. The system of claim 5, wherein at least one of the first mapping score or the second mapping score includes an indicator of data quantity.

7. The system of claim 5, wherein at least one of the first mapping score or the second mapping score includes an indicator of data quality.

8. The system of claim 7, wherein the indicator of data quality is defined based on an assessment of a number of biomarkers associated with the disease for which a biomarker to disease mapping is indicated in the data sources.

9. The system of claim 7, wherein the indicator of data quality is defined based on an assessment of an identity of biomarkers associated with the disease for which a biomarker to disease mapping is indicated in the data sources.

10. The system of claim 3, wherein the list is provided in rank order or alphabetical order.

11. The system of claim 2, wherein the system further comprises an analytics platform configured to interface with the data sources to selectively identify correlations based on analysis of contents of the data sources responsive to the query and a modeling component configured to apply a selected model, based on the query, to at least in part define the response.

12. A method of drug discovery, the method comprising:
accessing information associated with genetic markers from a data platform scalable to include a plurality of data sources, the data sources including at least a clinical research database providing matched data and not matched data from results of clinical trials;
employing a drug discovery module to analyze terabytes of data from the data sources to:
evaluate the matched data to define a mapping of drugs to biomarkers determined based on a first qualitative and quantitative assessment to have a first mapping score above a first threshold, and evaluate the not matched data to include at least some of the not matched data within the mapping of drugs to biomarkers determined based on the first qualitative and quantitative assessment to have the first mapping score above the first threshold; and employing the drug discovery module to:

evaluate the matched data to define a mapping of biomarkers to diseases determined based on a second qualitative and quantitative assessment to have second mapping score above a second threshold, and evaluate the not matched data to include at least some of the not matched data within the mapping of biomarkers to diseases determined based on the second qualitative and quantitative assessment to have the second mapping score above the second threshold, the drug discovery module comprising processing circuitry configured to provide a potential drug to disease link based on the mapping of drugs to biomarkers and the mapping of biomarkers to diseases using the biomarkers as a bridge between respective mappings, wherein the first and second mapping scores indicate a level of validation for each respective mapping.

13. The method of claim 12, further comprising receiving a query from a user, and generating a response to the query, the response providing the potential drug to disease link.

14. The method of claim 13, wherein the query defines a drug, a disease or a biomarker, and wherein the response defines a list of potential drug to disease links including the drug, the disease or the biomarker.

15. The method of claim 14, wherein the list is defined based on the potential drug to disease links that have a composite mapping score greater than a predefined threshold.

16. The method of claim 15, wherein the composite mapping score comprises the first mapping score for the mapping of drugs to biomarkers and the second mapping score for the mapping of biomarkers to diseases.

17. The method of claim 16, wherein at least one of the first mapping score or the second mapping score includes an indicator of data quantity.

18. The method of claim 16, wherein at least one of the first mapping score or the second mapping score includes an indicator of data quality.

19. The method of claim 18, wherein the indicator of data quality is defined based on an assessment of a number of biomarkers associated with the disease for which a biomarker to disease mapping is indicated in the data sources.

20. The method of claim 18, wherein the indicator of data quality is defined based on an assessment of an identity of biomarkers associated with the disease for which a biomarker to disease mapping is indicated in the data sources.

* * * * *